(12) United States Patent
Martinson et al.

(10) Patent No.: US 8,784,475 B2
(45) Date of Patent: *Jul. 22, 2014

(54) INSTRUMENTED IMPLANTABLE STENTS, VASCULAR GRAFTS AND OTHER MEDICAL DEVICES

(75) Inventors: James B. Martinson, Minnetonka, MN (US); John G. Stark, Deephaven, MN (US); Timothy J. B. Hanson, Plymouth, MN (US); Steven Backes, Minneapolis, MN (US)

(73) Assignee: IZEX Technologies, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/536,660

(22) Filed: Jun. 28, 2012

(65) Prior Publication Data

US 2012/0271200 A1 Oct. 25, 2012

Related U.S. Application Data

(62) Division of application No. 11/267,386, filed on Nov. 4, 2005, now Pat. No. 8,308,794.

(60) Provisional application No. 60/722,361, filed on Sep. 30, 2005, provisional application No. 60/628,050, filed on Nov. 15, 2004.

(51) Int. Cl.
| A61F 2/06 | (2013.01) |
| A61M 31/00 | (2006.01) |
| A61K 9/22 | (2006.01) |
| A61B 5/02 | (2006.01) |

(52) U.S. Cl.
USPC ............... 623/1.15; 604/93.01; 604/890.1; 600/505

(58) Field of Classification Search
USPC ............... 623/1.11, 1.12, 1.14, 1.15, 1.2; 604/93.01, 890.1–892.1; 600/504–507
See application file for complete search history.

(56) References Cited

U.S. PATENT DOCUMENTS

| 2,693,796 A | 11/1954 | Warner |
| 2,777,439 A | 1/1957 | Tuttle |

(Continued)

FOREIGN PATENT DOCUMENTS

| EP | 173161 A1 | 3/1986 |
| EP | 6689056 | 2/2004 |

(Continued)

OTHER PUBLICATIONS

U.S. Appl. No. 10/854,400, Final Office Action mailed Aug. 20, 2013, 13 pgs.

(Continued)

*Primary Examiner* — David Isabella
*Assistant Examiner* — Yashita Sharma
(74) *Attorney, Agent, or Firm* — Schwegman, Lundberg & Woessner, P.A.

(57) ABSTRACT

Several different smart stent structures are described for placement in vessel of a mammal. The stents can be advantageously used to perform measurements of the conditions in the vessel and transmit the measurements wireless out from the patient. In some embodiments, the stent performs therapy within the vessel and may be controlled with a microprocessor, which may or may not communicate wirelessly. Some implantable devices comprise a drug delivery system based, for example, on either a microelectromechanical structure or a cover that opens upon application of an electrical current. Smart devices can be used, for example, the detect deposits in a vessel, aneurysms in the vessel or other modifications of flow in the vessel.

15 Claims, 15 Drawing Sheets

(56) References Cited

U.S. PATENT DOCUMENTS

| | | |
|---|---|---|
| 2,832,334 A | 4/1958 | Whitelaw |
| 3,253,588 A | 5/1966 | Vuilleumier et al. |
| 3,373,992 A | 3/1968 | Ludeman |
| 3,374,675 A | 3/1968 | Michael |
| 3,495,824 A | 2/1970 | Cuinier |
| 3,521,623 A | 7/1970 | Nichols et al. |
| 3,667,457 A | 6/1972 | Zumaglini |
| 3,734,087 A | 5/1973 | Sayer et al. |
| 3,866,604 A | 2/1975 | Curless et al. |
| 3,929,335 A | 12/1975 | Malick et al. |
| 3,976,057 A | 8/1976 | Barclay |
| 3,986,498 A | 10/1976 | Lewis |
| 4,037,480 A | 7/1977 | Wagner |
| 4,039,039 A | 8/1977 | Gottfried |
| 4,135,503 A | 1/1979 | Romano |
| 4,178,923 A | 12/1979 | Curlee |
| 4,235,437 A | 11/1980 | Ruis et al. |
| 4,256,094 A | 3/1981 | Kapp et al. |
| 4,270,527 A | 6/1981 | Peters et al. |
| 4,306,571 A | 12/1981 | Mcleod, Jr. |
| 4,323,080 A | 4/1982 | Melhart |
| 4,331,133 A | 5/1982 | Arkans |
| 4,336,245 A | 6/1982 | Wason |
| 4,354,676 A | 10/1982 | Ariel |
| 4,375,217 A | 3/1983 | Arkans |
| 4,396,010 A | 8/1983 | Arkans |
| 4,397,308 A | 8/1983 | Hepburn |
| 4,407,496 A | 10/1983 | Johnson |
| 4,408,559 A | 10/1983 | Sugiura |
| 4,408,599 A | 10/1983 | Mummert |
| 4,419,988 A | 12/1983 | Mummert |
| 4,422,634 A | 12/1983 | Hopkins |
| 4,426,884 A | 1/1984 | Polchaninoff |
| 4,436,099 A | 3/1984 | Raftopoulos |
| 4,436,303 A | 3/1984 | McKillip |
| 4,485,808 A | 12/1984 | Hepburn |
| 4,501,148 A | 2/1985 | Nicholas et al. |
| 4,508,111 A | 4/1985 | Hepburn |
| 4,512,567 A | 4/1985 | Phillips |
| 4,520,804 A | 6/1985 | DiGeorge |
| 4,522,213 A | 6/1985 | Wallroth |
| 4,538,595 A | 9/1985 | Hajianpour |
| 4,538,600 A | 9/1985 | Hepburn |
| 4,544,154 A | 10/1985 | Ariel |
| 4,548,208 A | 10/1985 | Niemi |
| 4,553,124 A | 11/1985 | Malicki |
| 4,556,216 A | 12/1985 | Pitkanen |
| 173,161 A | 3/1986 | Townsend |
| 4,576,158 A | 3/1986 | Boland |
| 4,586,495 A | 5/1986 | Petrofsky |
| 4,590,925 A | 5/1986 | Dillon |
| 4,604,098 A | 8/1986 | Seamone et al. |
| 4,620,532 A | 11/1986 | Houswerth |
| 4,621,620 A | 11/1986 | Anderson |
| 4,624,246 A | 11/1986 | Ajemian |
| 4,645,199 A | 2/1987 | Bloemendaal |
| 4,651,719 A | 3/1987 | Funk et al. |
| 4,653,479 A | 3/1987 | Maurer |
| 4,654,010 A | 3/1987 | Havriluk |
| 4,681,097 A | 7/1987 | Pansiera |
| 4,697,808 A | 10/1987 | Larson et al. |
| 4,711,242 A | 12/1987 | Petrofsky |
| 4,716,889 A | 1/1988 | Saringer |
| 4,718,665 A | 1/1988 | Airy et al. |
| 4,757,453 A | 7/1988 | Nasiff |
| 4,762,134 A | 8/1988 | Gala |
| 4,763,901 A | 8/1988 | Richter |
| 4,785,674 A | 11/1988 | Orman et al. |
| 4,796,641 A | 1/1989 | Mills et al. |
| 4,801,138 A | 1/1989 | Airy et al. |
| 4,815,469 A | 3/1989 | Cohen et al. |
| 4,817,588 A | 4/1989 | Bledsoe |
| 4,822,336 A | 4/1989 | Ditraglia |
| 4,825,852 A | 5/1989 | Genovese et al. |
| 4,828,257 A | 5/1989 | Dyer et al. |
| 4,830,021 A | 5/1989 | Thornton |
| 4,836,218 A | 6/1989 | Gay et al. |
| 4,839,822 A | 6/1989 | Dormond et al. |
| 4,848,152 A | 7/1989 | Pratt, Jr. |
| 4,858,620 A | 8/1989 | Sugarman et al. |
| 4,863,157 A | 9/1989 | Mendel et al. |
| 4,875,469 A | 10/1989 | Brook et al. |
| 4,905,560 A | 3/1990 | Suzuki et al. |
| 4,909,262 A | 3/1990 | Halpern et al. |
| 4,912,638 A | 3/1990 | Pratt, Jr. |
| 4,913,163 A | 4/1990 | Roger et al. |
| 4,922,925 A | 5/1990 | Crandall et al. |
| 4,928,674 A | 5/1990 | Halperin et al. |
| 4,928,959 A | 5/1990 | Bassett et al. |
| 4,930,497 A | 6/1990 | Saringer |
| 4,934,694 A | 6/1990 | McIntosh |
| 4,944,288 A | 7/1990 | Rawcliffe |
| 4,952,928 A | 8/1990 | Carroll et al. |
| 4,958,632 A | 9/1990 | Duggan |
| 4,958,645 A | 9/1990 | Cadell et al. |
| 4,988,981 A | 1/1991 | Zimmerman et al. |
| 5,000,169 A | 3/1991 | Swicegood et al. |
| 5,003,965 A | 4/1991 | Talish et al. |
| 5,012,820 A | 5/1991 | Meyer |
| 5,013,037 A | 5/1991 | Stermer |
| 5,019,974 A | 5/1991 | Beckers |
| 5,020,795 A | 6/1991 | Airy et al. |
| 5,031,604 A | 7/1991 | Dye |
| 5,042,504 A | 8/1991 | Huberti |
| 5,050,618 A | 9/1991 | Larsen |
| 5,052,375 A | 10/1991 | Stark et al. |
| 5,052,379 A | 10/1991 | Airy et al. |
| 5,054,771 A | 10/1991 | Mansfield |
| 5,078,152 A | 1/1992 | Bond et al. |
| 5,090,421 A | 2/1992 | Wagoner, III |
| 5,116,296 A | 5/1992 | Watkins et al. |
| 5,121,747 A | 6/1992 | Andrews |
| 5,125,412 A | 6/1992 | Thornton |
| 5,133,732 A | 7/1992 | Wiktor |
| 5,135,536 A | 8/1992 | Hillstead |
| 5,153,584 A | 10/1992 | Engira |
| 5,178,160 A | 1/1993 | Gracovetsky et al. |
| 5,181,902 A | 1/1993 | Erickson et al. |
| 5,186,163 A | 2/1993 | Dye |
| 5,195,941 A | 3/1993 | Erickson et al. |
| 5,209,712 A | 5/1993 | Feri |
| 5,211,161 A | 5/1993 | Stef |
| 5,218,954 A | 6/1993 | Van Bemmelen |
| 5,227,874 A | 7/1993 | Von Kohorn |
| 5,239,987 A | 8/1993 | Kaiser et al. |
| 5,252,102 A | 10/1993 | Singer |
| 5,255,188 A | 10/1993 | Telepko |
| 5,263,491 A | 11/1993 | Thornton |
| 5,265,010 A | 11/1993 | Evans-Paganelli et al. |
| 5,280,265 A | 1/1994 | Kramer et al. |
| 5,280,783 A | 1/1994 | Focht et al. |
| 5,282,460 A | 2/1994 | Boldt |
| 5,284,131 A | 2/1994 | Gray |
| 5,287,546 A | 2/1994 | Tesic et al. |
| 5,297,540 A | 3/1994 | Kaiser et al. |
| 5,307,791 A | 5/1994 | Senoue et al. |
| 5,335,674 A | 8/1994 | Siegler |
| 5,336,245 A | 8/1994 | Adams et al. |
| 5,337,758 A | 8/1994 | Moore et al. |
| 5,338,157 A | 8/1994 | Blomquist |
| 5,354,162 A | 10/1994 | Burdea et al. |
| 5,360,392 A | 11/1994 | McCoy |
| 5,368,546 A | 11/1994 | Stark et al. |
| 5,373,852 A | 12/1994 | Harrison et al. |
| 5,391,141 A | 2/1995 | Hamilton |
| 5,396,896 A | 3/1995 | Tumey et al. |
| 5,410,472 A | 4/1995 | Anderson |
| 5,417,643 A | 5/1995 | Taylor |
| 5,425,750 A | 6/1995 | Moberg |
| 5,435,321 A | 7/1995 | Mcmillen et al. |
| 5,437,610 A | 8/1995 | Cariapa et al. |
| 5,437,617 A | 8/1995 | Heinz et al. |
| 5,443,440 A | 8/1995 | Tumey et al. |
| 5,452,205 A | 9/1995 | Telepko |

(56) References Cited

U.S. PATENT DOCUMENTS

| | | |
|---|---|---|
| 5,453,075 A | 9/1995 | Bonutti et al. |
| 5,462,504 A | 10/1995 | Trulaske et al. |
| 5,466,213 A | 11/1995 | Hogan et al. |
| 5,474,083 A | 12/1995 | Church et al. |
| 5,474,088 A | 12/1995 | Zaharkin et al. |
| 5,474,090 A | 12/1995 | Begun et al. |
| 5,476,441 A | 12/1995 | Durfee et al. |
| 5,484,389 A | 1/1996 | Stark et al. |
| 5,515,858 A | 5/1996 | Myllymaeki |
| 5,520,622 A | 5/1996 | Bastyr et al. |
| 5,538,005 A | 7/1996 | Harrison et al. |
| 5,553,609 A | 9/1996 | Chen et al. |
| 5,556,421 A | 9/1996 | Prutchi et al. |
| 5,558,627 A | 9/1996 | Singer et al. |
| 5,569,120 A | 10/1996 | Anjanappa et al. |
| 5,571,959 A | 11/1996 | Griggs |
| 5,579,378 A | 11/1996 | Arlinghaus, Jr. |
| 5,583,758 A | 12/1996 | McIlroy et al. |
| 5,586,067 A | 12/1996 | Gross et al. |
| 5,597,373 A | 1/1997 | Bond et al. |
| 5,625,882 A | 4/1997 | Vook |
| 5,651,763 A | 7/1997 | Gates |
| 5,662,693 A | 9/1997 | Johnson et al. |
| 5,671,733 A | 9/1997 | Raviv et al. |
| 5,683,351 A | 11/1997 | Kaiser et al. |
| 5,704,364 A | 1/1998 | Saltzstein et al. |
| 5,713,841 A | 2/1998 | Graham |
| 5,722,418 A | 3/1998 | Bro |
| 5,751,959 A | 5/1998 | Sato et al. |
| 5,754,121 A | 5/1998 | Ward et al. |
| 5,772,611 A | 6/1998 | Hocherman |
| 5,775,332 A | 7/1998 | Goldman |
| 5,778,618 A | 7/1998 | Abrams |
| 5,785,666 A | 7/1998 | Costello et al. |
| 5,788,618 A | 8/1998 | Joutras |
| 5,792,077 A | 8/1998 | Gomes |
| 5,792,085 A | 8/1998 | Walters |
| 5,801,756 A | 9/1998 | Iizawa |
| 5,823,975 A | 10/1998 | Stark et al. |
| 5,827,209 A | 10/1998 | Gross |
| 5,830,162 A | 11/1998 | Giovannetti |
| 5,836,304 A | 11/1998 | Kellinger et al. |
| 5,842,175 A | 11/1998 | Andros et al. |
| 5,843,120 A | 12/1998 | Israel et al. |
| 5,851,193 A | 12/1998 | Arikka et al. |
| 5,868,647 A | 2/1999 | Belsole |
| 5,882,203 A | 3/1999 | Correa et al. |
| 5,888,173 A | 3/1999 | Singhal |
| 5,890,997 A | 4/1999 | Roth |
| 5,908,383 A | 6/1999 | Brynjestad |
| 5,913,310 A | 6/1999 | Brown |
| 5,915,240 A | 6/1999 | Karpf |
| 5,918,603 A | 7/1999 | Brown |
| 5,929,782 A | 7/1999 | Stark et al. |
| 5,935,086 A | 8/1999 | Beacon et al. |
| 5,935,162 A | 8/1999 | Dang |
| 5,940,801 A | 8/1999 | Brown |
| 5,954,621 A | 9/1999 | Joutras et al. |
| 5,961,446 A | 10/1999 | Beller et al. |
| 5,980,435 A | 11/1999 | Joutras et al. |
| 5,980,447 A | 11/1999 | Trudeau |
| 5,989,157 A | 11/1999 | Walton |
| 5,997,476 A | 12/1999 | Brown |
| 6,007,459 A | 12/1999 | Burgess |
| 6,012,926 A | 1/2000 | Hodges et al. |
| 6,014,432 A | 1/2000 | Modney |
| 6,014,631 A | 1/2000 | Teagarden et al. |
| 6,029,138 A | 2/2000 | Khorasani et al. |
| 6,039,688 A | 3/2000 | Douglas et al. |
| 6,050,924 A | 4/2000 | Shea |
| 6,053,873 A | 4/2000 | Govari et al. |
| 6,059,506 A | 5/2000 | Kramer |
| 6,059,692 A | 5/2000 | Hickman |
| 6,119,516 A | 9/2000 | Hock |
| 6,123,861 A | 9/2000 | Santini et al. |
| 6,126,253 A | 10/2000 | Kelley et al. |
| 6,127,596 A | 10/2000 | Brown et al. |
| 6,129,663 A | 10/2000 | Ungless et al. |
| 6,132,337 A | 10/2000 | Krupka et al. |
| 6,140,697 A | 10/2000 | Usami et al. |
| 6,161,095 A | 12/2000 | Brown |
| 6,162,189 A | 12/2000 | Girone et al. |
| 6,162,253 A | 12/2000 | Conzemius et al. |
| 6,166,518 A | 12/2000 | Echarri et al. |
| 6,168,563 B1 | 1/2001 | Brown |
| 6,171,237 B1 | 1/2001 | Avitall et al. |
| 6,177,940 B1 | 1/2001 | Bond et al. |
| 6,183,259 B1 | 2/2001 | Macri et al. |
| 6,184,797 B1 | 2/2001 | Stark et al. |
| 6,190,287 B1 | 2/2001 | Nashner |
| 6,198,971 B1 | 3/2001 | Leysieffer |
| 6,206,829 B1 | 3/2001 | Iliff |
| 6,224,486 B1 | 5/2001 | Walker |
| 6,231,344 B1 | 5/2001 | Merzenich et al. |
| 6,246,975 B1 | 6/2001 | Rivonelli et al. |
| 6,248,065 B1 | 6/2001 | Brown |
| 6,249,809 B1 | 6/2001 | Bro et al. |
| 6,270,457 B1 | 8/2001 | Bardy |
| 6,272,481 B1 | 8/2001 | Lawrence et al. |
| 6,283,761 B1 | 9/2001 | Joao |
| 6,283,923 B1 | 9/2001 | Finkelstein et al. |
| 6,296,595 B1 | 10/2001 | Stark et al. |
| 6,302,844 B1 | 10/2001 | Walker et al. |
| 6,312,378 B1 | 11/2001 | Bardy |
| 6,322,502 B1 | 11/2001 | Schoenberg et al. |
| 6,371,123 B1 | 4/2002 | Stark et al. |
| 6,413,190 B1 | 7/2002 | Wood |
| 6,413,279 B1 | 7/2002 | Metzger et al. |
| 6,442,413 B1 | 8/2002 | Silver |
| 6,471,723 B1 | 10/2002 | Ashworth et al. |
| 6,475,477 B1 | 11/2002 | Kohn et al. |
| 6,491,666 B1 | 12/2002 | Santini, Jr. et al. |
| 6,515,593 B1 | 2/2003 | Stark et al. |
| 6,530,954 B1 | 3/2003 | Eckmiller |
| 6,531,417 B2 | 3/2003 | Choi et al. |
| 6,540,707 B1 | 4/2003 | Stark et al. |
| 6,563,464 B2 | 5/2003 | Ballantine et al. |
| 6,572,543 B1 | 6/2003 | Christopherson et al. |
| 6,610,069 B2 | 8/2003 | Euteneuer et al. |
| 6,638,231 B2 | 10/2003 | Govari et al. |
| 6,641,540 B2 | 11/2003 | Fleischman et al. |
| 6,676,706 B1 | 1/2004 | Mears et al. |
| 6,689,056 B1 | 2/2004 | Kilcoyne et al. |
| 6,695,866 B1 | 2/2004 | Kuehn et al. |
| 6,706,005 B2 | 3/2004 | Roy et al. |
| 6,718,163 B2 | 4/2004 | Tandy |
| 6,781,284 B1 | 8/2004 | Pelrine et al. |
| 6,783,260 B2 | 8/2004 | Machi et al. |
| 6,783,499 B2 | 8/2004 | Schwartz |
| 6,790,227 B2 | 9/2004 | Burgermeister |
| 6,821,299 B2 | 11/2004 | Kirking et al. |
| 6,827,670 B1 | 12/2004 | Stark et al. |
| 6,850,804 B2 | 2/2005 | Eggers et al. |
| 6,858,220 B2 | 2/2005 | Greenberg et al. |
| 6,872,187 B1 | 3/2005 | Stark et al. |
| 6,875,208 B2 | 4/2005 | Santini, Jr. et al. |
| 6,937,736 B2 | 8/2005 | Toda |
| 6,939,377 B2 | 9/2005 | Jayaraman et al. |
| 7,104,955 B2 | 9/2006 | Bardy |
| 7,117,028 B2 | 10/2006 | Bardy |
| 7,226,442 B2 | 6/2007 | Sheppard, Jr. et al. |
| 7,251,609 B1 | 7/2007 | McAlindon et al. |
| 7,416,537 B1 | 8/2008 | Stark et al. |
| 8,308,794 B2 | 11/2012 | Martinson et al. |
| 8,491,572 B2 | 7/2013 | Martinson et al. |
| 2002/0017834 A1 | 2/2002 | Macdonald |
| 2002/0029784 A1 | 3/2002 | Stark et al. |
| 2002/0177782 A1 | 11/2002 | Penner |
| 2002/0188282 A1 | 12/2002 | Greenberg |
| 2003/0032892 A1 | 2/2003 | Erlach et al. |
| 2003/0125017 A1 | 7/2003 | Greene et al. |
| 2003/0153819 A1 | 8/2003 | Lliff |
| 2003/0225331 A1 | 12/2003 | Diederich et al. |
| 2004/0034332 A1 | 2/2004 | Uhland |

(56) References Cited

U.S. PATENT DOCUMENTS

| | | | |
|---|---|---|---|
| 2004/0073175 | A1 | 4/2004 | Jacobson et al. |
| 2004/0102854 | A1 | 5/2004 | Zhu |
| 2004/0106963 | A1 | 6/2004 | Tsukamoto et al. |
| 2004/0143221 | A1 | 7/2004 | Shadduck |
| 2004/0172083 | A1 | 9/2004 | Penner |
| 2004/0176672 | A1 | 9/2004 | Silver et al. |
| 2004/0220552 | A1 | 11/2004 | Heruth et al. |
| 2004/0249675 | A1 | 12/2004 | Stark et al. |
| 2005/0054988 | A1 | 3/2005 | Rosenberg et al. |
| 2005/0113652 | A1 | 5/2005 | Stark et al. |
| 2005/0113904 | A1 | 5/2005 | Shank et al. |
| 2005/0187797 | A1 | 8/2005 | Johnson |
| 2005/0273170 | A1 | 12/2005 | Navarro et al. |
| 2006/0129050 | A1 | 6/2006 | Martinson et al. |
| 2006/0204532 | A1 | 9/2006 | John et al. |
| 2006/0244532 | A1 | 11/2006 | Trifonov et al. |
| 2006/0271112 | A1 | 11/2006 | Martinson et al. |
| 2007/0155588 | A1 | 7/2007 | Stark et al. |
| 2008/0040153 | A1 | 2/2008 | Davis, Jr. |
| 2008/0097143 | A1 | 4/2008 | Califorrni |
| 2010/0121160 | A1 | 5/2010 | Stark |
| 2012/0116806 | A1 | 5/2012 | Stark et al. |
| 2013/0066426 | A1 | 3/2013 | Martinson et al. |

FOREIGN PATENT DOCUMENTS

| | | | |
|---|---|---|---|
| GB | 2177603 | A | 1/1987 |
| JP | 4-44708 | A | 2/1992 |
| JP | 5-38684 | A | 2/1993 |
| JP | 5-146476 | A | 6/1993 |
| JP | 7-504102 | A | 5/1995 |
| JP | 3023228 | U | 4/1996 |
| JP | 9-84771 | A | 3/1997 |
| JP | 9-114671 | A | 5/1997 |
| NL | 7806327 | | 12/1979 |
| NL | 7806327 | A | 12/1979 |
| PK | 2001035473 | A1 | 5/2001 |
| SU | 1380747 | A1 | 3/1988 |
| SU | 1750681 | A1 | 7/1992 |
| WO | WO-9501769 | A2 | 1/1995 |
| WO | WO-9522307 | A1 | 8/1995 |
| WO | WO-9604848 | A1 | 2/1996 |
| WO | WO-9620464 | A1 | 7/1996 |
| WO | WO-9636278 | A1 | 11/1996 |
| WO | 9837926 | A1 | 9/1998 |
| WO | WO-9837926 | A1 | 9/1998 |
| WO | WO-9842257 | A1 | 10/1998 |
| WO | WO-0012041 | A2 | 3/2000 |
| WO | WO-0040171 | A2 | 7/2000 |
| WO | 01/26548 | A1 | 4/2001 |
| WO | WO-0126548 | A1 | 4/2001 |
| WO | WO-0135473 | A1 | 5/2001 |
| WO | WO-2004093725 | A2 | 11/2004 |
| WO | WO-2005046514 | A2 | 5/2005 |
| WO | WO-2005082452 | A1 | 9/2005 |
| WO | WO-2005084257 | A2 | 9/2005 |

OTHER PUBLICATIONS

U.S. Appl. No. 12/689,568, Response filed Sep. 20, 2013 to Non Final Office Action mailed May 23, 2013, 10 pgs.

U.S. Appl. No. 13/611,232, Non Final Office Action mailed Aug. 22, 2013, 5 pgs.

"Air back Spinal System", Product Literature, (1993), 4 pgs.

U.S. Appl. No. 09/329,880, Notice of Allowance mailed Mar. 15, 2001, 6 pgs.

U.S. Appl. No. 09/329,880, Notice of Allowance mailed Jun. 8, 2000, 3 pgs.

U.S. Appl. No. 09/329,880, Notice of Allowance mailed Oct. 29, 2001, 5 pgs.

U.S. Appl. No. 09/339,071, Final Office Action mailed Jul. 13, 2007, 9 pgs.

U.S. Appl. No. 09/339,071, Advisory Action mailed May 4, 2004, 3 pgs.

U.S. Appl. No. 09/339,071, Advisory Action mailed Jun. 7, 2006, 5 pgs.

U.S. Appl. No. 09/339,071, Advisory Action mailed Jul. 7, 2005, 3 pgs.

U.S. Appl. No. 09/339,071, Examiner Interview Summary mailed Apr. 7, 2004, 4 pgs.

U.S. Appl. No. 09/339,071, Examiner Interview Summary mailed Aug. 15, 2006, 3 pgs.

U.S. Appl. No. 09/339,071, Final Office Action mailed Jan. 25, 2006, 13 pgs.

U.S. Appl. No. 09/339,071, Final Office Action mailed Jan. 28, 2004, 13 pgs.

U.S. Appl. No. 09/339,071, Final Office Action mailed Aug. 27, 2002, 10 pgs.

U.S. Appl. No. 09/339,071, Final Office Action mailed Dec. 15, 2004, 13 pgs.

U.S. Appl. No. 09/339,071, Non Final Office Action mailed May 21,2003, 11 pgs.

U.S. Appl. No. 09/339,071, Non Final Office Action mailed Jun. 24, 2004, 8 pgs.

U.S. Appl. No. 09/339,071, Non Final Office Action mailed Aug. 2, 2005, 13 pgs.

U.S. Appl. No. 09/339,071, Non Final Office Action mailed Oct. 12, 2006, 8 pgs.

U.S. Appl. No. 09/339,071, Non Final Office Action mailed Nov. 15, 2007, 10 pgs.

U.S. Appl. No. 09/339,071, Non Final Office Action mailed Dec. 17, 2001, 8 pgs.

U.S. Appl. No. 09/339,071, Notice of Allowance mailed Apr. 23, 2009, 6 pgs.

U.S. Appl. No. 09/339,071, Preliminary Amendment filed Feb. 27, 2003, 9 pgs.

U.S. Appl. No. 09/339,071, Preliminary Amendment filed Sep. 25, 2006, 11 pgs.

U.S. Appl. No. 09/339,071, Preliminary Amendment filed Oct. 16, 2007, 10 pgs.

U.S. Appl. No. 09/339,071, Response filed Feb. 15, 2008 to Non Final Office Action mailed Nov. 15, 2007, 5 pgs.

U.S. Appl. No. 09/339,071, Response filed Apr. 15, 2004 to Final Office Action mailed Jan. 28, 2004, 8 pgs.

U.S. Appl. No. 09/339,071, Response filed Apr. 16, 2007 to Non Final Office Action mailed Oct. 12, 2006, 11 pgs.

U.S. Appl. No. 09/339,071, Response filed May 23, 2006 to Final Office Action mailed Jan. 25, 2006, 14 pgs.

U.S. Appl. No. 09/339,071, Response filed Jun. 17, 2002 to Non Final Office Action mailed Dec. 17, 2001, 7 pgs.

U.S. Appl. No. 09/339,071, Response filed Jun. 28, 2005 to Final Office Action mailed Dec. 15, 2004, 15 pgs.

U.S. Appl. No. 09/339,071, Response filed Jul. 3, 2000 to Restriction Requirement mailed Jun. 9, 2000, 2 pgs.

U.S. Appl. No. 09/339,071, Response filed Sep. 24, 2004 to Non Final Office Action mailed Jun. 24, 2004, 11 pgs.

U.S. Appl. No. 09/339,071, Response filed Nov. 2, 2005 to Non Final Office Action mailed Aug. 2, 2005, 12 pgs.

U.S. Appl. No. 09/339,071, Response filed Nov. 21, 2003 to Non Final Office Action mailed May 21, 2003, 11 pgs.

U.S. Appl. No. 09/339,071, Restriction Requirement mailed Jun. 9, 2000, 8 pgs.

U.S. Appl. No. 09/382,433, Amendment filed Jan. 23, 2003 in Response to Non-Final Office Action mailed Jul. 23, 2002, 8 pgs.

U.S. Appl. No. 09/382,433, Amendment filed Jun. 4, 2001 in Response to Non-Final Office Action mailed Feb. 28, 2001, 5 pgs.

U.S. Appl. No. 09/382,433, Amendment filed Jun. 18, 2002 in Response to Office Action mailed Jun. 3, 2002, 2 pgs.

U.S. Appl. No. 09/382,433, Amendment filed Jul. 23, 2004 in Response to Non-Final Office Action mailed Jan. 28, 2004, 11 pgs.

U.S. Appl. No. 09/382,433, Amendment filed Oct. 13, 2003 in Response to Non-Final Office Action mailed Apr. 11, 2003, 11 pgs.

U.S. Appl. No. 09/382,433, Amendment filed Nov. 30, 2000 in Response to Office Action mailed Nov. 20, 2000, 2 pgs.

U.S. Appl. No. 09/382,433, Final Office Action mailed Aug. 24, 2001, 7 pgs.

(56) References Cited

OTHER PUBLICATIONS

U.S. Appl. No. 09/382,433, Non-Final Office Action mailed Jan. 28, 2004, 9 pgs.

U.S. Appl. No. 09/382,433, Non-Final Office Action mailed Feb. 28, 2001, 7 pgs.

U.S. Appl. No. 09/382,433, Non-Final Office Action mailed Apr. 11, 2003, 13 pgs.

U.S. Appl. No. 09/382,433, Non-Final Office Action mailed Jul. 23, 2002, 5 pgs.

U.S. Appl. No. 09/382,433, Notice of Allowance mailed Sep. 8, 2004, 5 pgs.

U.S. Appl. No. 09/382,433, Office Action mailed Jun. 3, 2002, 4 pgs.

U.S. Appl. No. 09/382,433, Preliminary Amendment filed Feb. 25, 2002 in Response to Final Office Action mailed Aug. 24, 2001, 7 pgs.

U.S. Appl. No. 09/382,433, Restriction Requirement mailed Nov. 20, 2000, 8 pgs.

U.S. Appl. No. 09/416,192, 312 Amendment filed May 26, 2004, 7 pgs.

U.S. Appl. No. 09/416,192, Final Office Action mailed Jul. 2, 2002, 4 pgs.

U.S. Appl. No. 09/416,192, Final Office Action mailed Nov. 18, 2003, 5 pgs.

U.S. Appl. No. 09/416,192, Non Final Office Action mailed Mar. 7, 2003, 4 pgs.

U.S. Appl. No. 09/416,192, Non Final Office Action mailed Jul. 19, 2001, 4 pgs.

U.S. Appl. No. 09/416,192, Notice of Allowance mailed May 14, 2004, 5 pgs.

U.S. Appl. No. 09/416,192, PTO Response to 312 Amendment mailed Nov. 4, 2004, 2 pgs.

U.S. Appl. No. 09/416,192, Response filed Jan. 2, 2003 to Final Office Action mailed Jul. 2, 2002, 3 pgs.

U.S. Appl. No. 09/416,192, Response filed Jan. 17, 2002 to Non Final Office Action mailed Jul. 19, 2001, 4 pgs.

U.S. Appl. No. 09/416,192, Response filed Feb. 18, 2004 to Final Office Action mailed Nov. 18, 2003, 5 pgs.

U.S. Appl. No. 09/416,192, Response filed May 1, 2001 to Restriction Requirement mailed Mar. 27, 2001, 6 pgs.

U.S. Appl. No. 09/416,192, Response filed Sep. 8, 2003 to Non Final Office Action mailed Mar. 7, 2003, 3 pgs.

U.S. Appl. No. 09/416,192, Restriction Requirement mailed Mar. 27, 2001, 4 pgs.

U.S. Appl. No. 09/968,595, Advisory Action mailed Mar. 30, 2007, 3 pgs.

U.S. Appl. No. 09/968,595, Examiner Interview Summary filed Jul. 18, 2006, 3 pgs.

U.S. Appl. No. 09/968,595, Examiner Interview Summary mailed Oct. 10, 2008, 2 pgs.

U.S. Appl. No. 09/968,595, Examiner Interview Summary mailed Nov. 17, 2009, 3 pgs.

U.S. Appl. No. 09/968,595, Final Office Action mailed Jan. 8, 2007, 16 pgs.

U.S. Appl. No. 09/968,595, Final Office Action mailed Feb. 11, 2008, 14 pgs.

U.S. Appl. No. 09/968,595, Final Office Action mailed May 11, 2010, 22 pgs.

U.S. Appl. No. 09/968,595, Non Final Office Action mailed Mar. 23, 2006, 12 pgs.

U.S. Appl. No. 09/968,595, Non Final Office action mailed Jun. 3, 2009, 14 pgs.

U.S. Appl. No. 09/968,595, Non Final Office Action mailed Jun. 18, 2007, 18 pgs.

U.S. Appl. No. 09/968,595, Non Final Office Action mailed Jun. 27, 2008, 15 pgs.

U.S. Appl. No. 09/968,595, Non Final Office Action mailed Aug. 16, 2010, 27 pgs.

U.S. Appl. No. 09/968,595, Non Final Office Action mailed Oct. 26, 2009, 16 pgs.

U.S. Appl. No. 09/968,595, Preliminary Amendment filed Feb. 17, 2006, 6 pgs.

U.S. Appl. No. 09/968,595, Preliminary Amendment filed Feb. 17, 2006, 13 pgs.

U.S. Appl. No. 09/968,595, Preliminary Amendment filed Apr. 3, 2007, 13 pgs.

U.S. Appl. No. 09/968,595, Preliminary Amendment filed Jul. 1, 2005, 7 pgs.

U.S. Appl. No. 09/968,595, Preliminary Amendment filed Oct. 1, 2001, 16 pgs.

U.S. Appl. No. 09/968,595, Response filed Jan. 26, 2010 to Non Final Office Action mailed Oct. 26, 2009, 1 pg.

U.S. Appl. No. 09/968,595, Response filed Mar. 7, 2007 to Final Office Action mailed Jan. 8, 2007, 2 pgs.

U.S. Appl. No. 09/968,595, Response filed Apr. 11, 2008 to Final Office Action mailed Feb. 11, 2008, 10 pgs.

U.S. Appl. No. 09/968,595, Response filed Jul. 5, 2006 to Non Final Office Action mailed Mar. 23, 2006, 14 pgs.

U.S. Appl. No. 09/968,595, Response filed Jul. 12, 2010 to Final Office Action mailed May 11, 2010, 14 pgs.

U.S. Appl. No. 09/968,595, Response filed Jul. 30, 2009 to Non Final Office Action mailed Jun. 3, 2009, 12 pgs.

U.S. Appl. No. 09/968,595, Response filed Sep. 26, 2008 to Non Final Office Action mailed Jun. 27, 2008, 9 pgs.

U.S. Appl. No. 09/968,595, Response filed Oct. 4, 2007 to Non Final Office Action mailed Jun. 18, 2007, 2 pgs.

U.S. Appl. No. 09/968,595, Response filed Oct. 12, 2006 to Non Final Office Action mailed Oct. 6, 2006, 2 pgs.

U.S. Appl. No. 09/968,595, Supplemental Preliminary Amendment filed Feb. 28, 2006, 7 pgs.

U.S. Appl. No. 09/968,595, Supplemental Response to Non Final Office Action mailed Jun. 27, 2008, 11 pgs.

U.S. Appl. No. 10/403,650, Advisory Action mailed Mar. 15, 2010, 4 pgs.

U.S. Appl. No. 10/403,650, Advisory Action mailed Sep. 17, 2008, 3 pgs.

U.S. Appl. No. 10/403,650, Advisory Action mailed Oct. 2, 2009, 3 pgs.

U.S. Appl. No. 10/403,650, Examiner Interview Summary filed Oct. 20, 2009, 2 pgs.

U.S. Appl. No. 10/403,650, Final Office Action mailed Jun. 24, 2009, 7 pgs.

U.S. Appl. No. 10/403,650, Final Office Action mailed Jun. 27, 2008, 9 pgs.

U.S. Appl. No. 10/403,650, Final Office Action mailed Oct. 17, 2007, 7 pgs.

U.S. Appl. No. 10/403,650, Final Office Action mailed Nov. 25, 2009, 7 pgs.

U.S. Appl. No. 10/403,650, Non Final Office Action mailed Apr. 12, 2007, 11 pgs.

U.S. Appl. No. 10/403,650, Non Final Office Action mailed Nov. 15, 2005, 5 pgs.

U.S. Appl. No. 10/403,650, Non Final Office Action mailed Nov. 26, 2007, 8 pgs.

U.S. Appl. No. 10/403,650, Non Final Office Action mailed Dec. 24, 2008, 8 pgs.

U.S. Appl. No. 10/403,650, Preliminary Amendment filed Feb. 26, 2008, 10 pgs.

U.S. Appl. No. 10/403,650, Preliminary Amendment filed Sep. 22, 2008, 10 pgs.

U.S. Appl. No. 10/403,650, Preliminary Amendment filed Oct. 30, 2007, 9 pgs.

U.S. Appl. No. 10/403,650, Response filed Jan. 25, 2010 to Final Office Action mailed Nov. 25, 2009, 10 pgs.

U.S. Appl. No. 10/403,650, Response filed Feb. 15, 2006 to Non final Office Action mailed Nov. 15, 2005, 9 pgs.

U.S. Appl. No. 10/403,650, Response filed Mar. 24, 2009 to Non Final office Action mailed Dec. 24, 2008, 9 pgs.

U.S. Appl. No. 10/403,650, Response filed Jul. 28, 2005 to Restriction Requirement mailed Jul. 12, 2005, 2 pgs.

U.S. Appl. No. 10/403,650, Response filed Aug. 10, 2007 to Non final Office Action mailed Apr. 12, 2007, 11 pgs.

U.S. Appl. No. 10/403,650, Response filed Aug. 24, 2009 to Non final Office Action mailed Jun. 24, 2009, 11 pgs.

(56) References Cited

OTHER PUBLICATIONS

U.S. Appl. No. 10/403,650, Response filed Aug. 25, 2008 to Final Office Action mailed Jun. 27, 2008, 10 pgs.
U.S. Appl. No. 10/403,650, Restriction Requirement mailed Jul. 12, 2005, 5 pgs.
U.S. Appl. No. 10/819,092, Final Office Action mailed Jan. 9, 2008, 11 pgs.
U.S. Appl. No. 10/819,092, Final Office Action mailed Mar. 13, 2009, 11 pgs.
U.S. Appl. No. 10/819,092, Final Office Action mailed Sep. 28, 2009, 13 pgs.
U.S. Appl. No. 10/819,092, Non Final Office Action mailed Sep. 3, 2008, 11 pgs.
U.S. Appl. No. 10/819,092, Preliminary Amendment filed Jul. 10, 2009 to Final Office Action mailed Mar. 13, 2009, 9 pgs.
U.S. Appl. No. 10/819,092, Response filed Mar. 10, 2008 to Final Office Action mailed Jan. 9, 2008, 10 pgs.
U.S. Appl. No. 10/819,092, Response filed Jun. 9, 2008 to Restriction Requirement mailed May 12, 2008, 6 pgs.
U.S. Appl. No. 10/819,092, Response filed Dec. 3, 2008 to Non Final Office Action mailed Sep. 3, 2008, 8 pgs.
U.S. Appl. No. 10/819,092, Restriction Requirement mailed May 12, 2008, 6 pgs.
U.S. Appl. No. 10/845,400, Response filed Dec. 22, 2010 to Non Final Office mailed Jun. 22, 2010, 7 pgs.
U.S. Appl. No. 10/854,400, Response filed Jan. 11, 2012 to Non Final Office Action mailed Oct. 11, 2011, 7 pgs.
U.S. Appl. No. 10/854,400, Advisory Action mailed Apr. 6, 2010, 2 pgs.
U.S. Appl. No. 10/854,400, Final Office Action mailed Jan. 19, 2010, 11 pgs.
U.S. Appl. No. 10/854,400, Final Office Action mailed Mar. 14, 2011, 11 pgs.
U.S. Appl. No. 10/854,400, Non Final Office Action mailed Jun. 22, 2010, 10 pgs.
U.S. Appl. No. 10/854,400, Non Final Office Action mailed Jul. 9, 2009, 12 pgs.
U.S. Appl. No. 10/854,400, Non Final Office Action mailed Oct. 11, 2011, 9 pgs.
U.S. Appl. No. 10/854,400, Preliminary Amendment filed May 26, 2004, 2 pgs.
U.S. Appl. No. 10/854,400, Response filed Mar. 23, 2010 to Final Office Action mailed Jan. 19, 2010, 6 pgs.
U.S. Appl. No. 10/854,400, Response filed Jul. 14, 2011 to Final Office Action mailed Mar. 14, 2011, 7 pgs.
U.S. Appl. No. 10/854,400, Response filed Oct. 2, 2009 to Non Final Office Action mailed Jul. 9, 2009, 13 pgs.
U.S. Appl. No. 10/997,737, Advisory Action mailed Aug. 29, 2008, 3 pgs.
U.S. Appl. No. 10/997,737, Advisory Action mailed Dec. 5, 2006, 3 pgs.
U.S. Appl. No. 10/997,737, Amendment filed Jun. 8, 2009 in Response to Non Final Office Action mailed Mar. 16, 2009, 12 pgs.
U.S. Appl. No. 10/997,737, Examiner Interview Summary mailed Jan. 19, 2010, 2 pgs.
U.S. Appl. No. 10/997,737, Examiner Interview Summary mailed Oct. 31, 2007, 2 pgs.
U.S. Appl. No. 10/997,737, Final Office Action mailed Feb. 20, 2008, 10 pgs.
U.S. Appl. No. 10/997,737, Final Office Action mailed Jun. 10, 2008, 11 pgs.
U.S. Appl. No. 10/997,737, Final Office Action mailed Oct. 24, 2006, 6 pgs.
U.S. Appl. No. 10/997,737, Non Final Office Action mailed Mar. 16, 2009, 7 pgs.
U.S. Appl. No. 10/997,737, Non Final Office Action mailed Jun. 27, 2006, 12 pgs.
U.S. Appl. No. 10/997,737, Non Final Office Action mailed Oct. 29, 2008, 8 pgs.
U.S. Appl. No. 10/997,737, Preliminary Amendment filed Feb. 21, 2007, 9 pgs.
U.S. Appl. No. 10/997,737, Preliminary Amendment filed Nov. 24, 2004, 3 pgs.
U.S. Appl. No. 10/997,737, Response filed Jan. 11, 2008 to Non Final Office Action mailed Jul. 24, 2007, 14 pgs.
U.S. Appl. No. 10/997,737, Response filed Apr. 4, 2008 to Final Office Action mailed Feb. 20, 2008, 11 pgs.
U.S. Appl. No. 10/997,737, Response filed Jun. 13, 2008 to Final Office Action mailed Jun. 10, 2008, 11 pgs.
U.S. Appl. No. 10/997,737, Response filed Sep. 10, 2009 to Non Final Office Action mailed Mar. 16, 2009, 15 pgs.
U.S. Appl. No. 10/997,737, Response filed Sep. 27, 2006 to Non Final Office Action mailed Jun. 27, 2006, 7 pgs.
U.S. Appl. No. 10/997,737, Response filed Oct. 17, 2007 to Restriction Requirement mailed Jul. 24, 2007, 14 pgs.
U.S. Appl. No. 10/997,737, Response filed Nov. 10, 2006 to Final Office Action mailed Oct. 24, 2006, 10 pgs.
U.S. Appl. No. 10/997,737, Response filed on Dec. 12, 2008 to Non Final Office Action mailed Oct. 29, 2008, 11 pgs.
U.S. Appl. No. 10/997,737, Restriction Requirement mailed Jul. 24, 2007, 10 pgs.
U.S. Appl. No. 11/017,593, Final Office Action mailed Sep. 6, 2006, 10 pgs.
U.S. Appl. No. 11/017,593, Non Final Office Action mailed Sep. 7, 2005, 7 pgs.
U.S. Appl. No. 11/017,593, Response filed Feb. 7, 2006 to Non Final Office Action mailed Sep. 7, 2005, 11 pgs.
U.S. Appl. No. 11/017,593, Response filed May 12, 2006 to Restriction Requirement mailed Apr. 18, 2006, 7 pgs.
U.S. Appl. No. 11/017,593, Restriction Requirement mailed Apr. 18, 2006, 4 pgs.
U.S. Appl. No. 11/267,386, Advisory Action mailed May 22, 2009, 3 pgs.
U.S. Appl. No. 11/267,386, Advisory Action mailed Jun. 4, 2010, 3 pgs.
U.S. Appl. No. 11/267,386, Advisory Action mailed Jun. 16, 2009, 3 pgs.
U.S. Appl. No. 11/267,386, Examiner Interview Summary filed Sep. 8, 2009, 2 pgs.
U.S. Appl. No. 11/267,386, Final Office Action mailed Mar. 10, 2009, 8 pgs.
U.S. Appl. No. 11/267,386, Final Office Action mailed Mar. 30, 2010, 11 pgs.
U.S. Appl. No. 11/267,386, Final Office Action mailed Jul. 7, 2009, 10 pgs.
U.S. Appl. No. 11/267,386, Final Office Action mailed Aug. 19, 2011, 13 pgs.
U.S. Appl. No. 11/267,386, Non Final Action mailed Sep. 29, 2009, 10 pgs.
U.S. Appl. No. 11/267,386, Non Final Office Action mailed Jun. 17, 2008, 10 pgs.
U.S. Appl. No. 11/267,386, Non Final Office Action mailed Nov. 29, 2010, 11 pgs.
U.S. Appl. No. 11/267,386, Notice of Allowance mailed Mar. 29, 2012, 10 pgs.
U.S. Appl. No. 11/267,386, Preliminary Amendment filed Jun. 10, 2009, 6 pgs.
U.S. Appl. No. 11/267,386, Request for Continued Examination filed Jun. 10, 2009, 6 pgs.
U.S. Appl. No. 11/267,386, Response filed Jan. 18, 2012 to Final Office Action mailed Aug. 19, 2011, 7 pgs.
U.S. Appl. No. 11/267,386, Response filed May 1, 2008 to Non Final Office Action mailed Apr. 2, 2008, 6 pgs.
U.S. Appl. No. 11/267,386, Response filed May 7, 2009 to Final Office Action mailed Mar. 10, 2009, 6 pgs.
U.S. Appl. No. 11/267,386, Response filed May 20, 2010 to Final Office Action mailed Mar. 30, 2010, 7 pgs.
U.S. Appl. No. 11/267,386, Response filed May 27, 2011 to Non Final Office Action mailed Nov. 29, 2010, 7 pgs.
U.S. Appl. No. 11/267,386, Response filed May 28, 2009 to Advisory Action mailed May 22, 2009, 2 pgs.

(56) References Cited

OTHER PUBLICATIONS

U.S. Appl. No. 11/267,386, Response filed Sep. 17, 2008 to Non Final Office Action mailed Jun. 17, 2008, 8 pgs.
U.S. Appl. No. 11/267,386, Response filed Dec. 29, 2009 to Non Final Office Action mailed Sep. 29, 2009, 6 pgs.
U.S. Appl. No. 11/267,386, Supplemental Notice of Allowability mailed May 9, 2012, 7 pgs.
U.S. Appl. No. 11/267/386, Non Final Office Action mailed Apr. 2, 2008, 10 pgs.
U.S. Appl. No. 11/494,719, Advisory Action mailed Jan. 23, 2008, 3 pgs.
U.S. Appl. No. 11/494,719, Advisory Action mailed Mar. 25, 2009, 3 pgs.
U.S. Appl. No. 11/494,719, Examiner Interview Summary mailed Feb. 23, 2010, 3 pgs.
U.S. Appl. No. 11/494,719, Examiner Interview Summary mailed Aug. 27, 2009, 2 pgs.
U.S. Appl. No. 11/494,719, Final Office Action mailed Jan. 8, 2009, 7 pgs.
U.S. Appl. No. 11/494,719, Final Office Action mailed Nov. 8, 2007, 8 pgs.
U.S. Appl. No. 11/494,719, Final Office Action mailed Nov. 16, 2009, 8 pgs.
U.S. Appl. No. 11/494,719, Non Final Action mailed Mar. 28, 2008, 9 pgs.
U.S. Appl. No. 11/494,719, non Final Office Action mailed May 30, 2007, 9 pgs.
U.S. Appl. No. 11/494,719, Non Final Office Action mailed Jun. 30, 2009, 7 pgs.
U.S. Appl. No. 11/494,719, Notice of Allowance mailed Apr. 18, 2012, 8 pgs.
U.S. Appl. No. 11/494,719, Response filed Jan. 8, 2008 to Final Office Action mailed Nov. 8, 2007, 11 pgs.
U.S. Appl. No. 11/494,719, Response filed Feb. 18, 2010 to Final Office Action mailed Nov. 16, 2009, 10 pgs.
U.S. Appl. No. 11/494,719, Response filed Mar. 9, 2009 to Final Office Action mailed Jan. 8, 2009, 9 pgs.
U.S. Appl. No. 11/494,719, Response filed Jun. 25, 2008 to Non Final Office Action mailed Mar. 28, 2008, 13 pgs.
U.S. Appl. No. 11/494,719, Response filed Aug. 30, 2007 to Non Final Office Action mailed May. 30, 2007, 2 pgs.
U.S. Appl. No. 11/494,719, Response filed Sep. 1, 2009 to Non Final Office Action mailed Jun. 30, 2009, 10 pgs.
U.S. Appl. No. 11/494,719, Response filed Oct. 13, 2008 to Restriction Requirement mailed Sep. 12, 2008, 6 pgs.
U.S. Appl. No. 11/494,719, Restriction Requirement mailed Sep. 12, 2008, 7 pgs.
U.S. Appl. No. 11/714,669, Final Office Action mailed Sep. 13, 2011, 11 pgs.
U.S. Appl. No. 11/714,669, Non Final Office Action mailed Nov. 9, 2010, 9 pgs.
U.S. Appl. No. 11/714,669, Preliminary Amendment filed Mar. 6, 2007, 2 pgs.
U.S. Appl. No. 11/714,669, Response filed Jan. 12, 2012 to Final Office Action mailed Sep. 13, 2011, 8 pgs.
U.S. Appl. No. 11/714,669, Response filed May 9, 2011 to Non Final Office Action mailed Nov. 9, 2010, 8 pgs.
U.S. Appl. No. 12/689,568, Final Office Action mailed Apr. 25, 2012, 9 pgs.
U.S. Appl. No. 12/689,568, Non Final Offic Action mailed Sep. 8, 2011, 22 pgs.
U.S. Appl. No. 12/689,568, Preliminary Amendment filed Jan. 19, 2010, 5 pgs.
U.S. Appl. No. 12/689,568, Response Filed Feb. 8, 2012 to Non-Final Office Action Received Sep. 8, 2011, 11 pgs.
U.S. Appl. No. 12/689,568, Response filed Feb. 8, 2012 to Non Final Office Action mailed Sep. 8, 2011, 11 pgs.
U.S. Appl. No. 12/689,568, Response filed Jun. 29, 2011 to Restriction Requirement mailed May 31, 2011, 8 pgs.
U.S. Appl. No. 12/689,568, Restriction Requirement mailed May 31, 2011, 7 pgs.
U.S. Appl. No. 13/184,289, Non Final Office Action mailed Jun. 8, 2012, 16 pgs.
U.S. Appl. No. 10/854,400, Final Office Action mailed May 24, 2012, 10 pgs.
Chinese Application Serial No. 99812468.0, First Office Action issued Jul. 25, 2003, (w/ English Translation), 10 pgs.
"Clinical Biomechanicals of the Spine", 2nd Edition, (1990), 482.
"Clinical Biomechanics of the Spine", 2nd Edition, (1990), p. 482.
Europeam Application No. 99966681.1, Supplementary Search Report mailed Sep. 8, 2004, 6 pgs.
European Application Serial No. 05822048, Supplementary European Search Report mailed Mar. 5, 2009, 6 pgs.
European Application Serial No. 05822048.4, Supplementary European Search Report mailed Mar. 24, 2009, 12 pgs.
European Application Serial No. 96920238.1, Supplementary Partial European Search Report mailed Nov. 21, 2002, 5 pgs.
European Application Serial No. 98915149.3, Supplementary Partial European Search Report dated Apr. 1, 2003, 5 pgs.
European Application Serial No. 98915149.3, Supplementary Partial European Search Report mailed Jul. 11, 2003, 5 pgs.
European Application Serial No. 99966681.1, Office Action mailed Jan. 9, 2009, 5 pgs.
European Application Serial No. 99966681.1, Office Action mailed Feb. 7, 2006, 5 pgs.
European Application Serial No. 99966681.1, Office Action mailed Mar. 11, 2005, 3 pgs.
European Application Serial No. 99966681.1, Office Action mailed Sep. 11, 2007, 5 pgs.
European Application Serial No. 99966681.1, Reply filed Apr. 14, 2008 to Office Action mailed Sep. 11, 2007, 7 pgs.
European Application Serial No. 99966681.1, Reply filed Jun. 19, 2006 to Office Action mailed Feb. 7, 2006, 11 pgs.
European Application Serial No. 99966681.1, Response filed Jul. 21, 2005 to Office Action mailed Mar. 11, 2005, 3 pgs.
European Application Serial No. 99966681.1, Response filed Jul. 23, 2004 to Partial European Search Report mailed Jun. 14, 2004, 4 pgs.
European Application Serial No. 99966681.1, Supplementary Partial European Search Report, 6 pgs.
International Application Serial No. PCT/US00/15888, International Preliminary Examination Report mailed Jul. 23, 2001, 43 pgs.
International Application Serial No. PCT/US00/15888, International Search Report mailed Aug. 21, 2000, 2 pgs.
International Application Serial No. PCT/US00/16859, International Preliminary Examination Report mailed Dec. 2, 2002, 8 pgs.
International Application Serial No. PCT/US00/16859, International Search Report and Written Opinion mailed Oct. 16, 2000, 8 pgs.
International Application Serial No. PCT/US00/16859, International Search Report mailed Oct. 16, 2000, 7 pgs.
International Application Serial No. PCT/US00/16859, Written Opinion mailed Oct. 19, 2001, 6 pgs.
International Application Serial No. PCT/US00/26990, International Preliminary Examination Report mailed Oct. 24, 2001, 4 pgs.
International Application Serial No. PCT/US00/26990, International Search Report mailed Dec. 27, 2000, 3 pgs.
International Application Serial No. PCT/US05/41021, International Search Report mailed Jan. 25, 2007, 1 pg.
International Application Serial No. PCT/US05/41021, Written Opinion mailed Jan. 25, 2007, 3 pgs.
International Application Serial No. PCT/US05/41339, International Search Report and Written Opinion mailed Jun. 20, 2006, 9 pgs.
International Application Serial No. PCT/US2005/41339, International Search Report mailed Jun. 20, 2006, 3 pgs.
International Application Serial No. PCT/US2005/41339, Written Opinion mailed Jun. 20, 2006, 6 pgs.
International Application Serial No. PCT/US96/07047, International Preliminary Examination Report mailed Sep. 4, 1997, 5 pgs.
International Application Serial No. PCT/US96/07047, International Search Report mailed Oct. 2, 1996, 7 pgs.
International Application Serial No. PCT/US96/07047, Written Opinion mailed May 22, 1997, 4 pgs.

(56) References Cited

OTHER PUBLICATIONS

International Application Serial No. PCT/US98/05600, International Preliminary Examination Report mailed Jun. 16, 1999, 7 pgs.
International Application Serial No. PCT/US98/05600, International Search Report mailed Jul. 9, 1998, 6 pgs.
International Application Serial No. PCT/US98/05600, Written Opinion mailed Jan. 27, 1999, 6 pgs.
International Application Serial No. PCT/US99/19935, Article 34 Amendment filed Nov. 17, 2000, 19 pgs.
International Application Serial No. PCT/US99/19935, International Preliminary Examination Report mailed Feb. 26, 2001, 23 pgs.
International Application Serial No. PCT/US99/19935, International Search Report mailed Mar. 24, 2000, 6 pgs.
International Application Serial No. PCT/US99/19935, Written Opinion mailed Sep. 19, 2000, 7 pgs.
International Application Serial No. PCT/US99/31030, International Preliminary Examination Report mailed Jun. 12, 2001, 8 pgs.
International Application Serial No. PCT/US99/31030, International Search Report Jul. 13, 2000, 5 pgs.
International Application Serial No. PCT/US99/31030, Written Opinion mailed Dec. 13, 2000, 7 pgs.
Japanese Application Serial No. 2000-567165, Office Action mailed Apr. 9, 2009, (English Translation), 3 pgs.
Japanese Application Serial No. 2000-591930, Argument and Amendment filed Feb. 26, 2008 filed in Response to Office Action mailed Nov. 27, 2007, 4 pgs.
Japanese Application Serial No. 2000-591930, Decision of Refusal mailed Mar. 25, 2008, (w/ English Translation), 3 pgs.
Japanese Application Serial No. 2000-591930, Official Action mailed Nov. 27, 2007, (English Translation), 3 pgs.
Japanese Application Serial No. 545857/98, Amendment and Argument filed Jan. 9, 2007, 11 pgs.
Japanese Application Serial No. 545857/98, Appeal Brief and Amendment filed Jun. 25, 2007, 10 pgs.
Japanese Application Serial No. 545857/98, Final Rejection mailed Mar. 26, 2007, (English Translation), 2 pgs.
Japanese Application Serial No. 545857/98, Office Action mailed Aug. 17, 2006, (English Translation), 6 pgs.
Machine Translation of JP 58-109212, 24 pgs.
"Masterhinge Shoulder Brace 3", Product Literature by, Johnson & Johnson Professional, Inc.
"Newport Shoulder System", Literature by, Orthodmerica Products, Inc., (1996).
"Put Your Patient's Recovery Steps Ahead with the Sutter CPM 9000", Sutter Biomedical Inc., SUT 133, V85, (Jan. 1985), 1-6.
"Thera-Kinetics Product Literature", (1994), 26 pgs.
"Upper Extremities and Back Product Literature", Smith & Nephew DonJoy, Inc. Rev., (May 1996).
Allington, R, et al., "Strengthening Techniques of the Quadriceps Muscles: An Electromyographic Evaluation", Journal of the American Therapy Association vol. 66, No. 11, (1966), 1173-1176.
Antich, T J, et al., "Modification of Quadriceps Femoris Muscle Exercises During Knee Rehabilitation", Physical Therapy, 66(8), (1986), 1246-1251.
Baumeister, T, et al., "Standard Handbook for Mechanical Engineers, 8th ed.", McGraw-Hill Book Company, New York, NY, (1978), p. 16-8.
Biering-Sorenson, F., "A One-Year Prospective Study of Low Back Trouble in a General Population", Danish Medical Bulletin, 31(5), (Oct. 1984), 362-375.
During, J., et al., "Toward Standards for Posture—Postural Characteristics of the Lower Back System in Normal and Pathologic Conditions", Spine, 10(1), (1985), 83-87.
Elnagger, I. M., et al., "Effects of Spinal Flexion and Extension Exercises on Low-Back Pain and Spinal Mobility in Chronic Mechanical Low-Back Pain Patients", Spine, 16(8), (1991), 967-972.
Gough, J, et al., "An Investigation Into the Effectiveness of Various Forms of Quadriceps Exercises", Physiotherapy, 57(8),, (1971), 356-361.
Haberichter, P. A., et al., "Muscle Pressure Effects on Motorneuron Excitability", (Abstract R-224), Physical Therapy, 65(5), (1985), p. 723.
Hapgood, Fred, "Let Your Fingers Do the Talking", INC—Magazine for Growing Companies, vol. 19, Iss. 17, (Nov. 18, 1997), 119-120.
Henry, F M, et al., "Relationships Between Individual is Strength, Speed, and Mass in an Arm Movement", The Research Quarterly vol. 31. No. 1, (1989), 24-33.
Ibrahim, A., "Communicating in real-time on-line", New Straits Times, Kuala Lumpar, (Nov. 6, 1997), 5 pgs.
Kishino, N. D., et al., "Quantification of Lumbar Function—Part 4: Isometric and Isokinetic Lifting Simulation in Normal Subjects and Low-Back Dysfunction Patients", Spine, 10(10), (1985), 921-927.
Knapik, J., et al., "Angular Specificity and Test Mode Specificity of Isometric and Isokinetic Strength Testing", The Journal of Orthopedic and Sports Physical Therapy, 5(2), (1983), 58-65.
Krebs, D., et al., "Knee Joing Angle: Its Relationship to Quadriceps Femoris Activity in Normal and Postarthrotomy Limbs", Arch Phys Med. Rehabil., vol. 64, (1983), 441-447.
Leib, et al., "The Journal of Bone and Joint Surgery", vol. 53-A(4)., (1971), 749-758.
Lieb, F. J., et al., "Quadriceps Function—An Electromyographic Study Under Isometric Conditions", The Journal of Bone and Joint Surgery, vol. 53-A(4),, (1971), 749-758.
Lindh, M., "Increase of Muscle Strength From Isomeric Quadriceps Exercises at Different knee Angles", Scand J Rehab Med., II(1), (1979), 33-36.
Mayer, T. G, et al., "A prospective short-term study of chronic low back pain patients utilizing novel objective functional measurement", Pain, 25(1), (Apr. 1986), 53-68.
Mayer, T. G., et al., "Quantification of Lumbar Function—Part 2: Sagittal Plane Trunk Strength in Chronic Low-Back Pain Patients", Spine, 10(8), (1985), 765-772.
Million, R., et al., "Assessment of the progress of the back-pain patient 1981 Volvo Award in Clinical Science", Spine, 7(3), (May-Jun. 1982), 204-12.
Pollock, M. L., et al., "Chapter 22—Muscle", In: Rehabiliation of the Spine: Science and Practice, Hochschuler, S., et al., Editors, Mosby-Year Book, Inc., (1993), 263-284.
Rasch, P. J., "Progressive Resistance Exercise: Isotonic and Isometric: A Review", The Journal of the Association for Physical and Mental Rehabilitation, 15(2), (1961), 46-50.
Sikorski, J. M., et al., "A Rationalized Approach to Physiotherapy for Low-Back Pain", Spine, 10(6), (1985), 571-579.
Skurja, Jr., M., et al., "Quadriceps Action in Straight Leg Raise Versus Isolated Knee Extension", EMG and Tension Study, Physical Therapy, 60, (1980), p. 582.
Smidt, G., et al., "Assessment of Abdominal and Back Extensor Function—A Quantitative Approach and Results for Chronic Low-Back Patients", Spine, 8(2), (1983), 211-219.
Soderberg, G. L., et al., "An Electromyographic Analysis of Quadriceps Femoris Muscle Setting and Straight Leg Raising", Physical Therapy, 63(9), (1983), 1434-1438.
Soderberg, G. L., et al., "Electromyographic Analysis of Knee Exercises in Healthy Subjects and in Patients with Knee Pathologies", Physical Therapy, 67(11), (1987), 1691-1696.
Stark, John G, "An Orthopedic Device Supporting Two or More Treatment Systems and Associated methodsM", Application Serial No. 96/36278, (Nov. 21, 1996).
Stratford, P, "Electromyography of the Quadriceps Femoris Muscles in Subjects with Normal Knees", Physical Therapy, 62(3), (1981), 279-283.
Wild, J. J., et al., "Patellar Pain and Quadriceps Rehabilitation—An EMG Study", The American Journal of Sports Medicine, 10(1), (1982), 12-15.
U.S. Appl. No. 11/714,669 , Response filed Oct. 7, 2013 to Non Final Office Action mailed Jun. 7, 2013, 9 pgs.
U.S. Appl. No. 11/714,669, Notice of Allowance mailed Nov. 5, 2013, 10 pgs.
U.S. Appl. No. 13/184,289 , Response filed Oct. 17, 2013 to Non Final Office Action mailed Jun. 21, 2013, 12 pgs.
U.S. Appl. No. 13/184,289, Examiner Interview Summary mailed Oct. 15, 2013, 2 pgs.

(56) References Cited

OTHER PUBLICATIONS

U.S. Appl. No. 13/611,232, Preliminary Amendment filed Sep. 12, 2012, 3 pgs.
U.S. Appl. No. 13/611,232, Supplemental Preliminary Amendment filed Feb. 18, 2013, 7 pgs.
U.S. Appl. No. 10/854,400, Response filed Apr. 29, 2013 to Non Final Office Action mailed Jan. 31, 2013, 11 pgs.
U.S. Appl. No. 10/854,400, Decision on Pre-Appeal Brief Request mailed Oct. 23, 2012, 2 pgs.
U.S. Appl. No. 10/854,400, Examiner Interview Summary mailed Apr. 15, 2013, 3 pgs.
U.S. Appl. No. 10/854,400, Non Final Office Action mailed Jan. 31, 2013, 14 pgs.
U.S. Appl. No. 10/854,400, Pre-Appeal Brief Request filed Sep. 24, 2012, 5 pgs.
U.S. Appl. No. 11/267,386, Notice of Allowability mailed Oct. 5, 2012, 2 pgs.
U.S. Appl. No. 11/267,386, Supplemental Notice of Allowability mailed Jul. 18, 2012, 4 pgs.
U.S. Appl. No. 11/714,669, Final Office Action mailed Aug. 12, 2009, 8 pgs.
U.S. Appl. No. 11/714,669, Non Final Office Action mailed May 13, 2010, 6 pgs.
U.S. Appl. No. 11/714,669, Non Final Office Action mailed Aug. 1, 2008, 8 pgs.
U.S. Appl. No. 11/714,669, Non Final Office Action mailed Nov. 13 2009, 6 pgs.
U.S. Appl. No. 11/714,669, Response filed Jul. 1, 2010 to Non Final Office Action mailed Nov. 13, 2009, 8 pgs.
U.S. Appl. No. 11/714,669, Response filed Oct. 13, 2009 to Final Office Action mailed Aug. 12, 2009, 7 pgs.
U.S. Appl. No. 11/714,669, Response filed Nov. 3, 2008 to Non Final Office Action mailed Aug. 1, 2008, 8 pgs.
U.S. Appl. No. 11/714,669, Response filed Dec. 14, 2009 to Non Final Office Action mailed Nov. 13, 2009, 6 pgs.
U.S. Appl. No. 12/689,568, Final Office Action mailed Dec. 20, 2012, 20 pgs.
U.S. Appl. No. 12/689,568, Pre-Appeal Brief Request filed Sep. 25, 2012, 5 pgs.
U.S. Appl. No. 13/184,289, Final Office Action mailed Dec. 7, 2012, 22 pgs.
U.S. Appl. No. 13/184,289, Preliminary Amendment filed Jan. 20, 2012, 8 pgs.
U.S. Appl. No. 13/184,289, Response filed Nov. 5, 2012 to Non Final Office Action mailed Jun. 8, 2012, 13 pgs.
U.S. Appl. No. 13/184,289, Pre-Appeal Brief Request filed Mar. 6, 2013, 4 pgs.
U.S. Appl. No. 11/494,719, Notice of Allowance mailed May 29, 2013, 9 pgs.
U.S. Appl. No. 11/714,669, Non Final Office Action mailed Jun. 7, 2013, 10 pgs.
U.S. Appl. No. 12/689,568, Non Final Office Action mailed May 23, 2013, 23 pgs.
U.S. Appl. No. 13/184,289, Decision on Pre-Appeal Brief Request mailed Apr. 9, 2013, 2 pgs.
U.S. Appl. No. 13/184,289, Non Final Office Action mailed Jun. 21, 2013, 26 pgs.
U.S. Appl. No. 13/184,289, Response filed May 9, 2013 to Final Office Action mailed Dec. 7, 2012, 13 pgs.

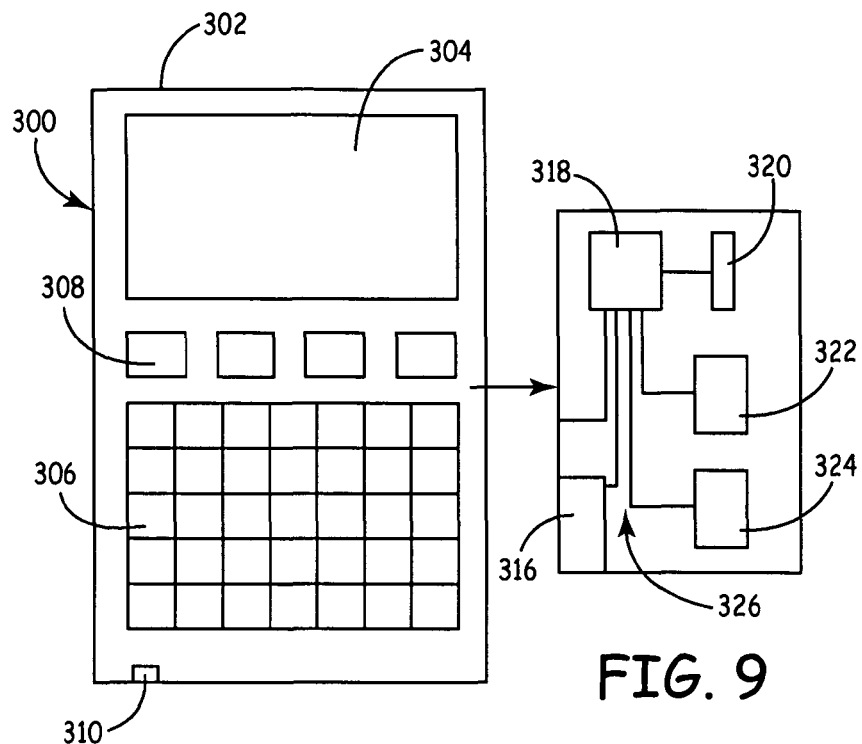
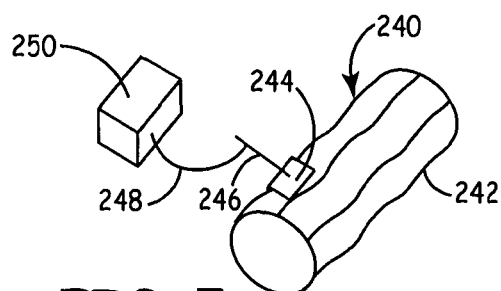
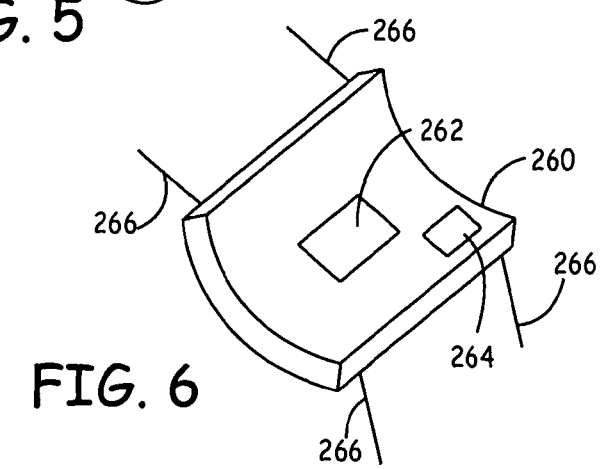

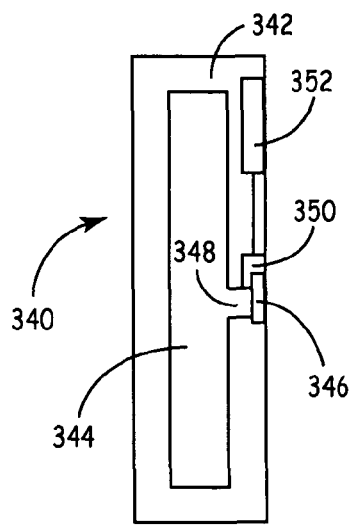
FIG. 10
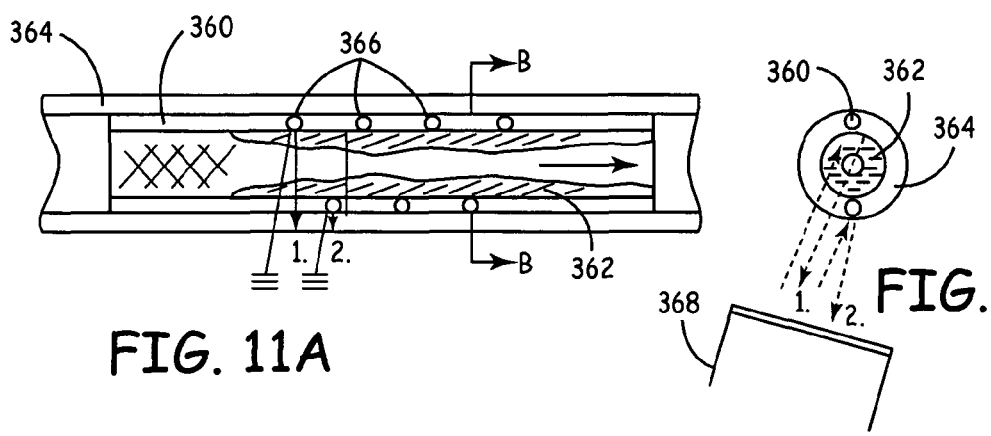
FIG. 11A
FIG. 11B

INSTRUMENTED IMPLANTABLE STENTS, VASCULAR GRAFTS AND OTHER MEDICAL DEVICES

CROSS REFERENCE TO RELATED APPLICATIONS

This application is a divisional application of U.S. patent application Ser. No. 11/267,386, filed Nov. 4, 2005, which claims priority to U.S. Provisional Patent Application, 60/722,361, filed on Sep. 30, 2005 to Stark et al., entitled "Instrumented Implantable Stents And Other Medical Devices," and U.S. Provisional Patent Application 60/628,050, filed on Nov. 15, 2004 to Stark et al., entitled "Instrumented Implantable Medical Devices," both of which are incorporated herein by reference.

FIELD OF THE INVENTION

The invention relates to a new generation of implantable medical devices, in particular stents, that provide treatment functions and/or detection functions within a compact format that allows placement in a range of locations within a patient.

BACKGROUND OF THE INVENTION

Innovative approaches have presented considerable opportunity to revolutionize medicine through providing more automated and/or remote treatment options in a variety of contexts. The objectives are to provide improved care and accelerated treatment delivery while increasing efficiency to keep costs down. With two way communication channels, the medical professionals can be apprised of the patient's condition without an office visit or invasive procedure, and medical devices can be remotely reprogrammed.

In an orthopedic treatment context, physical therapy can be performed, monitored and/or administered remotely relative to the clinician. An instrumented orthopedic system can prompt the patient for therapy, monitor the therapy, warn the patient of any dangerous conditions and/or record the patient's performance of the therapy for compliance monitoring and protocol evaluation. The instrumented orthopedic system can be designed to download therapy performance data with or without initial evaluation and/or upload protocol reprogramming. Suitable orthopedic parameters related to rehabilitation include, for example, stresses, range of motion, exerted energy levels, pulse, blood pressure, and the like.

Another area of significant remote monitoring and evaluation involves implantable cardiac devices. In particular, implantable pacemakers and cardiac defibrillators have been designed to transmit parameters external to the patient's body for communication to health care professionals, e.g. the appropriate physician. Functions relating to device operation can be communicated.

SUMMARY OF THE INVENTION

In a first aspect, the invention pertains to a stent comprising a support structure, a sensor or sensors and an implantable wireless communication system. The support structure comprises a biocompatible material with a structure suitable for placement within a mammalian vessel without significantly blocking flow. The sensor(s) is attached to the support structure. The implantable wireless communication system is operably connected to the sensor(s) such that data from the sensor can be transmitted with the wireless communication system. Suitable sensors include, for example, a sensor comprising a pressure sensor, an acoustic sensor, an accelerometer, a capacitor, an induction coil, resistors within a bridge structure, a vibration detector, a Doppler shift detector or combinations thereof. In some embodiments, the communication system is electrically connected to the sensor but is not physically connected to the support structure.

In a further aspect, the invention pertains to an implantable medical device comprising an implantable scaffold, a reservoir and a microelectromechanical delivery system. The reservoir comprises a bioactive agent and is attached to the implantable scaffold. The microelectromechanical delivery system is attached to the implantable scaffold and controls elution from the reservoir.

In another aspect, the invention pertains to a stent comprising a support structure, a reservoir and a control system. The frame comprises a biocompatible material with a structure suitable for placement within a mammalian vessel without significantly blocking flow. The reservoir comprises a bioactive agent and is operably connected to the support structure. The control system is operably connected to the reservoir to control the release of the bioactive agent from the reservoir. In some embodiments, the reservoir comprises a cover with a material dissolvable upon exposure to an electrical current, and the control system comprises a microprocessor with memory and a conduction pathway configured to deliver a current to dissolve the cover material under instructions from the microprocessor, and a plurality of such reservoirs can be included in the stent that are separately controlled to independently dissolve the cover material of each reservoir. The bioactive agent can comprise an antimicrobial agent, a hormone, a cytokine, a growth factor, a hormone releasing factor, a transcription factor, an infectious agent or vector, an anti-thrombogenic agent, an anti-restenosis agent, a calcium channel blocker, an antirestenosis agent, a blood pressure reducing agent, an ionic forms thereof, an unmixed combination thereof or a mixture thereof.

In other aspects, the invention pertains to a stent comprising a support structure, a power source and a surface. The support structure comprises a biocompatible material with a structure suitable for placement within a mammalian vessel without significantly blocking flow. The surface is configured to be charged by the power source at least over a portion of the surface, and the surface is supported by the frame. The power source can be an implanted battery or a system that received external energy through RF, magnetic or other electromagnetic source. In some embodiments, the surface comprises an inner surface and an outer surface that can be charged with a positive or negative charge. In alternative embodiments, the surface comprises an inner surface that can be charged positive and an outer surface that can be charged negative, or an inner surface that can be charged negative and an outer surface that can be charged positive. In some embodiments, the power source can be recharged through an antenna. The power source can comprise a battery.

Moreover, the invention pertains to a stent comprising a support structure, a microprocessor and a transducer. The support structure comprises a biocompatible material with a structure suitable for placement within a mammalian vessel without significantly blocking flow. The transducer is operably connected to the microprocessor. In some embodiments, the transducer is an electrical induction coil, although other suitable transducers are broadly described herein. In some embodiments, the stent may further comprise a power supply that is operably connected to the induction coil such that the power supply can be recharged, and in some embodiments the microprocessor is powered with electrical current generated with the induction coil. In other embodiments, the stent may further comprise a power supply in which the microprocessor is configured to measure the current induced in the coil with a magnetic or electromagnetic field.

In additional aspects, the invention pertains to a stent comprising an expandable structure with a generally cylindrical shape suitable for placement within a vessel. The expandable structure has a plurality of layers that can be selectively removed in the expanded configuration while leaving the remaining layer(s). In some embodiment, the plurality of layers is three layers. In other embodiments, at least one layer has a lever connected to the particular layer.

Furthermore, the invention pertains to a method for performing measurements within a mammalian vessel, e.g., a tissue with a lumen. The method comprises transmitting from an implanted device a measurement of a sensor within the vessel. The implanted device does not have any external physical connections.

In further aspects, the invention pertains to a method for performing a treatment within a mammalian vessel. The method comprises actuating an output transducer to perform the treatment. The transducer is deployed within the vessel without any external physical connections. The output transducer can be associated with a stent.

Also, the invention pertains to a medical device comprising a sensor and an ambulatory transmitter operably connected to the sensor. In general, the sensor can perform a measurement of skin or tissue motion that varies if an aneurysm is present. In some embodiments, the sensor is designed for contact mounting on a patient's skin. In further embodiment, the sensor is attached to an article that can be worn by the patient. In other embodiments, the medical device further comprises a biocompatible material associated with the sensor and transmitter to form an implantable structure that can be placed in the vicinity of a blood vessel.

In general, the various stent embodiments can be similarly adapted for forming similar structures within a prosthetic vessel, i.e., a biocompatible vessel suitable for implantation as a shunt or replacement vessel. For example, in other aspects, the invention pertains a biocompatible vessel suitable for implantation comprising a generally tubular material having a central lumen and a wireless communication system operably connected with the generally tubular material.

In further embodiments, the invention pertains to a central server comprising a processor connected to a communication channel. The communication channel is connected to an instrumented stent implanted within a patient. The communication channel can be connected, for example, to an internet connection, a WiFi connection, a satellite communication channel, a mobile phone connection or a combination thereof. The processor can be further connected to additional communication channels, as described further below, and to one or more databases, as described further below.

BRIEF DESCRIPTION OF THE DRAWINGS

FIG. 5 is a schematic perspective view of a third embodiment of a smart implantable stent.

FIG. 6 is a schematic perspective view of a fourth embodiment of a smart implantable stent.

FIG. 9 is a top view of hand held computer/personal digital assistant for patient use to interface with a medical device and/or a remote central server, with an insert on the right schematically depicting the interconnections of electrical components.

FIG. 10 is a sectional view of a MEMS based drug delivery system with the section taken through the center of the MEMS device.

FIG. 11A is a sectional side view of a stent deployed in a blood vessel that sensitive to visualization through ultrasound.

FIG. 11B is a sectional end view of the deployed stent of FIG. 11A taken along the line B-B of FIG. 11A and with the interaction with an ultrasound device depicted schematically.

DETAILED DESCRIPTION OF THE INVENTION

Figure 1:
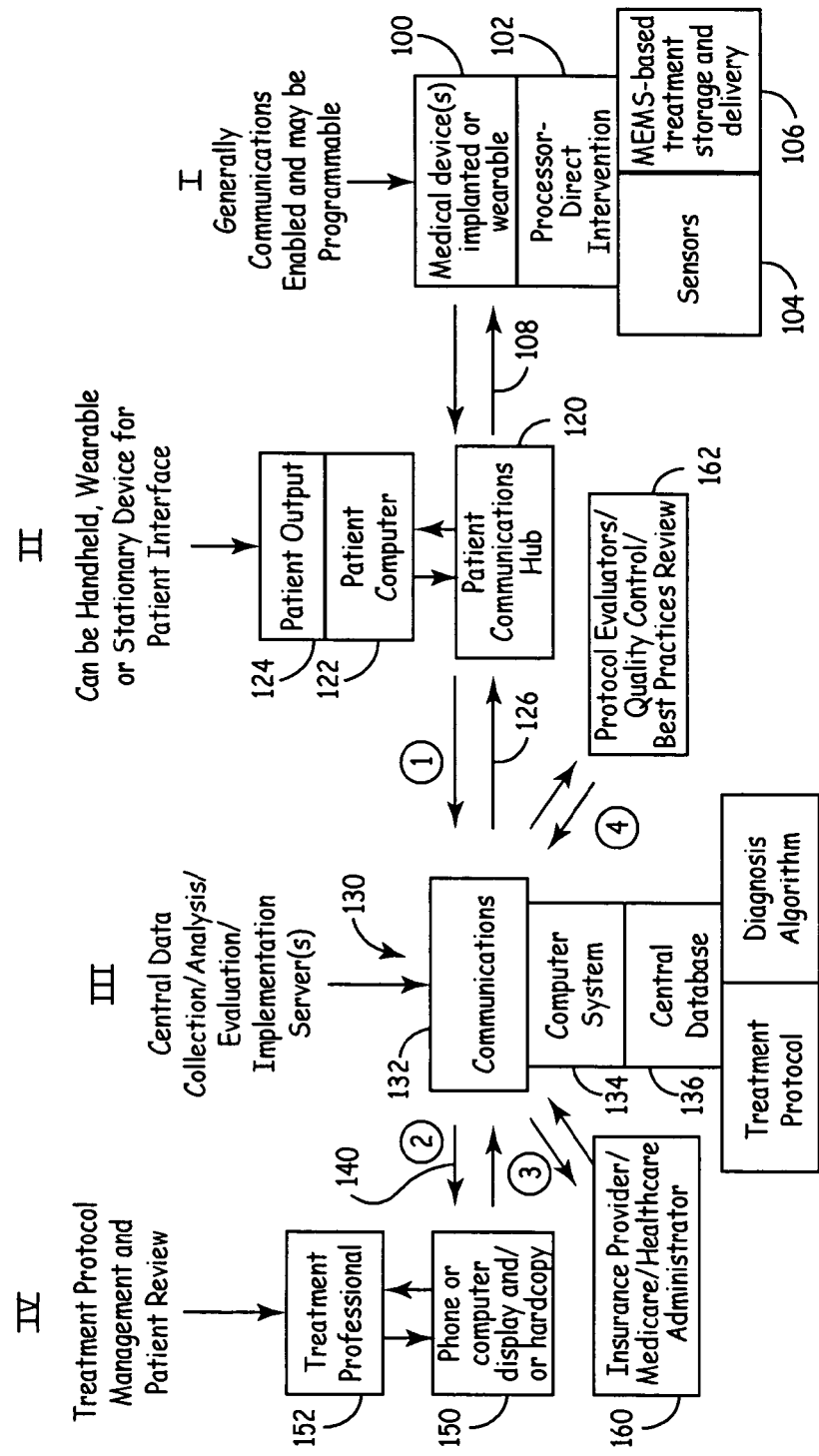
FIG. 1 is a schematic diagram depicting the components of smart/remote medical treatment system displaying the interaction of a medical device, a patient computer, a central server/database and medical professionals.

Smart stent structures and other small implantable medical devices can incorporate a miniature processor to coordinate functions associated with sensing, electrical, and/or electromechanical components of the device. The devices can be used for monitoring bodily functions, for drug delivery and/or for other treatment delivery approaches. Similarly, devices can be installed within and/or on the wall of a prosthetic vessel such that the devices can be operated following implantation of the prosthetic vessel. The processor associated with a stent, prosthetic vessel or other small implantable device can facilitate and/or adjust the function of a treatment structure associated with the implantable device and/or facilitate the performance of measurements. In some embodiments, the implantable devices have the ability to communicate exterior to a patient following implantation within a patient. This communication ability provides for transmission of measurements taken from within the body to an outside receiver for processing and/or to mediate treatments provided through the implantable device. Similarly, communication to the implanted structures provide for modifications of treatments within the patient implemented by the implanted structure, generally through the programming/reprogramming of the device. The communication into and from the patient generally can be mediated by a local communication system. However, either directly or indirectly, it is desirable for the communication in one or both directions from/to the implantable device and a remote communication system. The remote communication system can be associated with a remote central server(s) and corresponding databases. In addition, the remote communication system can facilitate communication between the implantable device/local communication system and a remote health care professional and/or insurance providers, reviewers, regulators and the like.

Due to instrumentation of the devices, the implantable devices can provide new functionalities within an implanted device to provide corresponding improved treatment options and/or diagnostic abilities. Improved diagnostic abilities can be based one or more measurement capabilities incorporated into the measurement device. Treatment structures can be interpreted broadly to cover structures that provide drugs or therapeutic forces to the surrounding environment within the patient. In some embodiments, microelectromechanical structures facilitate drug delivery from a stent or other small implantable structure. Furthermore, implantable power sources can be used to induce charged surfaces on the implant to influence the interaction of the surface with the native environment within the patient, although the device can be built without a power source if suitable components can be used to obtain power from sources external to the patient.

Available miniaturization approaches can be used to make very small smart devices that are controlled in some sense with a microprocessor. In some embodiments, the implantable device comprises a transducer. The transducer can be configured to produce electrical signals in response to conditions at the device, i.e., to make measurements within the patient, or the transducer can be configured to respond to electrical signals from an internal power source to induce a response, such as movement. Movement or other actuation of a transducer within the device can be used to deliver treatment such as drug delivery, to inhibit plaque deposition, accelerate revascularization, stabilize aberrant signals and/or to induce an alternative treatment function.

Similarly, communication systems can be made very small. These devices can be integrated directly onto the implanted medical device in some embodiments and may be integrated with the processor/controller. Small power systems are available for low power consumption applications, and auxiliary devices are available to recharge an implanted power system from outside of the body or to provide all of the power requirements to the implanted device from exterior to the patient.

In some embodiments of particular interest, it is desirable to interface the smart implantable devices with remote health care professionals to facilitate treatment and monitoring with fewer office visits. While remote monitoring can be advantageous with direct communication to health care professionals, there can be significant advantages in mediating communication through a central system, which can comprise one or more servers along with corresponding databases/distributed databases. Communication can be through radio transmission, phone transmission, satellite transmission, or the like or a combination thereof, and can be directed through the World Wide Web and corresponding Internet service, or more generally through some similar, possibly secure, private or public local or wide area communications network, such as a WiFi network or cellular network, at some stage in the transmission process.

Automation through a central server, generally with a corresponding medical database, can be used to communicate with a large number of patients along with a large number of clinicians to coordinate the treatment, outcomes monitoring, billing and other functions. Automation can also involve self-correction and/or automatic shut down and the like such that response time can be shortened to provide more effective response to changing conditions. The central server can also be used to facilitate and evaluate the fundamental selection of treatment protocols, and improve selection and/or design of treatment protocols through the analysis of a large number of treatment results to improve treatment outcomes as well as reduce costs through efficiencies. Description of medical databases and central servers is provided further in U.S. Pat. No. 6,827,670 to Stark et al., entitled "System For Medical Protocol Management" and WO 00/40171 A to Oyen et al., entitled "Remote Monitoring of an Instrumented Orthosis," both of which are incorporated herein by reference. In some embodiments, the implantable devices can be reprogrammed, either by the clinician or automatically/dynamically by a processor using an appropriate algorithm, to alter their function through protocol adjustments and the like.

The improved devices described herein expand the capabilities for remote medical treatment in several dimensions. In some embodiments, therapeutic delivery is moderated by instrumentation within implantable devices, for example, based on miniaturized components. In additional embodiments, stents can be instrumented to provide desirable monitoring functions and/or therapy management, active restenosis avoidance or active stenosis treatment. A particular implanted medical device/system can comprise components to perform the particular functions that may be physically attached within a monolithic structure or otherwise connected, physically near each other or positioned remotely from each other to yield a desired result, in which nonattached elements may be connected physically, such as with a wire or the like, or electromagnetically for wireless communication. In some embodiments, the devices can be designed to communicate, to be controlled and/or to be powered externally using micro scale, generally radio-frequency (RF), communication systems and appropriate corresponding power systems. Communication enabled devices can be tied to appropriate communication channels for remote transmission of the measurements as well as reprogramming of the device from a remote location. The communication channel can proceed through a central database that coordinates treatment and monitoring functions for a plurality of patients and a plurality of health care professionals. Thus, the system can be used to coordinate communication and transfer of data between health care professionals, patients, insurers, regulators and others involved in the administration of health care.

More specifically, in some embodiments, the medical treatment system can have an implanted medical device optionally with its own processor and/or its own communication elements, and a local controller, for example, a personal digital assistant or the like, that can communicate with the implanted medical device as well as with a remote computer(s) connected to a suitable communication channel. Remote communication can be performed through access to a remote communication channel, for example, through a hardwire connection or through wireless communication. The remote "computer" can be a central server or set of servers that maintain a central database or a distributed database, or it can be a computer at the site of a treating health care professional. For convenience, central server refers to one or a set or servers, and central database refers to a single database or a distributed network of databases, containing a plurality of data representations and/or modalities. The central server can provide access by a number of patients as well as a number of health care professionals and/or insurance carriers and/or regulator agencies. Thus, the system forms a multilayered hub and spoke model with the central server and/or central database at the hub and each layer corresponding to patient's, health care providers, insurers, regulators, etc., respectively. Similarly, the implantable device and its externally related elements, may be configured or broken into elements to alternatively amplify and transmit a raw signal, raw data, processed data, data from memory, Built In Test (BIT) data, data under specific contingent situations of the body's parameters, the device's parameters, data describing specific actions of the device, or combinations thereof.

With respect to implantable devices generally, in some embodiments the devices comprise of one or more sensors generally with a corresponding transducer(s). The transducers can reduce an analog or other physical parameter signal associated with the sensor that can be subsequently converted into a digital or other electrical signal suitable for further processing if appropriate. The electrical signal can be transmitted from the body to an external receiver, for example, using wireless communication. In some representative embodiments of interest, the signals are stored for transmission at a later time, although the signals can be transmitted intermittently without any prompting. In general, the implantable device may have a microprocessor, an appropriate power source and appropriate memory to mediate the interface between the transmitter and the sensor. In some embodiments, the implantable device can further include a receiver. Other embodiments have an output transducer that propagates energy in response to an electrical signal, which correspondingly may be generated in response to a biological condition, a radio transmission and electromagnetic signal or other biological or physical condition.

Drug or other chemical delivery for various implants can be facilitated through the use of micro-electromechanical systems (MEMS). In some embodiments, these drug elution devices can be programmed to deliver the therapeutic agent under prescribed conditions, with or without clinician intervention. For example, the drug delivery rate can be according to a programmed rate, such as a constant rate or a rate that is varied in a systematic way. Alternatively, the drug delivery parameters can be established within the device based on measurements within the device or an associated device. For example, the parameters related to drug elution rate may be physical parameter, for example, blood pressure, pulse rate or other similar parameter, or a chemical parameter, such as pH, oxygen concentration or serum glucose concentration. In some embodiments, the drug elution can be controlled through external stimulation or programming through transmitted instructions. In addition, a patient treatment protocol controlling the drug delivery rate can be occasionally evaluated, and the device's dispensing program can be reprogrammed through wireless communication with the implanted device. In some embodiments, the drug can only be dispensed upon receipt of an external signal providing an instruction to dispense the drug. In other embodiments, the action may be triggered directly in response to body chemistry, activation of a switch or through a computer algorithm.

Stents, as described herein refer to devices that insert within a vessel of the body such that flow in the vessel is maintained or improved. Stents of particular interest are stents suitable for placement within a blood vessel, lymphatic vessel, such as a lymphatic vein, reproductive vessel or the urinary tract vessel. Stents in various contexts have found considerable commercial acceptance and high clinical value. Drug coated stents are commercially available for use in coronary arteries. Specifically, commercial stents include, for example, the pacitaxel eluting Taxus™ stent from Boston Scientific and the sirolimus eluting Cypher™ stent from Johnson & Johnson. Other stents are available for placement in other vessels.

In general, stents can be used to open the vessel at the site of a blockage or partial blockage. Alternatively or additionally, a stent can be implanted solely to introduce functionality associated with the stent, such as a measuring/monitoring capability or treatment capability, at the location of the stent. In addition to commercial drug coatings, stents can be coated with metals, such as silver or platinum, that introduce, respectively, an antimicrobial effect and catalytic effects. As described herein, the stents can have measurement capabilities that are communicated external to the patient using communication channels described herein. In addition, the stents can have the capability to direct treatment of local or systemic conditions, for example, using one or more of the approaches described herein. Furthermore, through an appropriate communication channel the stent measurement and/or treatment functions can be reprogrammed from external to the body either at the direction of a physician, in response to feedback from a patient and/or due to monitoring by a local control apparatus or a central server. In some embodiments as described herein, instrumented stents comprise instrumentation that make measurements, absorb energy, emit energy, provides for controlled release of a drug or the like.

Available drug coatings are based on chemical elution. As described above, MEMS devices and other microelectrical devices can be used to control drug elution electronically or physically, such as through electrical, magnetic or other means/combination of means. In some embodiments, the electrical current can be used to stimulate drug release either through a MEMS effect or by initiating the biodegradation of a polymer. These approaches can be adapted for use with a stent.

For metal stents, the entire stent can function as an induction coil for receiving an RF signal. Thus, the stent can function as an antenna. The stent as an antenna can be electrically connected to suitable transmitter and/or receiver. In addition, the electromagnetic interaction with a metal coil stent can be used to direct an electric current in association with the stent. This can be used, for example, to recharge a battery or to direct a current into tissue or to directly power a device such as a pacing or defibrillation device. The field applied to the coil can be a static field or an oscillating field, such as an RF field. A magnetic field can be applied with the large magnets of an MRI instrument or the like.

In general, all of the structures described herein for incorporation into stents can be similarly directly incorporated into synthetic vessels that can be used to replace diseased or damaged vessels in the patient and/or as shunts to bypass diseased or damaged or blocked vessels, such as in coronary arteries. As described further below, prosthetic vessels can be formed from tissue-based materials and/or synthetic polymers or the like or combinations thereof. Transducers, processors, communication systems and/or other desirable device components can be assembled with the prosthetic vessels. The ability to interface the components with the prosthetic vessels prior to implantation can simplify the procedure as well as provide increased versatility relative to stents deployed within living vessel. In particular, components can easily be assembled with certain components on the exterior of the vessel that interface, for example, with electrical connections with transducers and the like along the interior wall of the vessel. More intricate connections can be formed in a clean facility with skilled technicians than can easily be performed by a clinician during the pressure of a medical procedure with the patient possibly under sedation or anesthesia.

For use with implantable devices, physical constraints on the systems provide performance guidelines for the electronics used to control the device. With respect to the power consumption if batteries are used, very thin batteries can be formed, as described further in published PCT application WO 01/35473A to Buckley et al., entitled "Electrodes Including Particles of Specific Sizes," incorporated herein by reference. These thin batteries can extend over a significant fraction of the device surface to extend the capacity of the battery. Also, if battery storage is used, the battery can be recharged using an RF signal to supply power to the device. See, for example, U.S. Pat. No. 6,166,518 to Guillermo et al., entitled "Implantable Power Management System," and Published U.S. Application 2004/0106963A to Tsukamoto et al., entitled "Implantable Medical Power Module," both of which are incorporated herein by reference.

Small radio frequency antennas can be used, or in some embodiments the antenna function can be the primary function of the device. Suitable antenna are described, for example, in U.S. Pat. No. 6,563,464 to Ballantine et al., entitled "Integrated On-chip Half-Wave Dipole Antenna Structure," and U.S. Pat. No. 6,718,163 to Tandy, entitled "Method of Operating Microelectronic Devices, and Methods of Providing Microelectronic Devices," both of which are incorporated herein by reference. Currently, the Federal Communication Commission has set aside a frequency band between 402 and 405 MHz specifically for wireless communication between implanted medical devices and external equipment. Based on the description above, the RF antenna can be incorporated on the chip with the processor and the battery can be integrated into a device with the chip. Suitable sensors and the like are described further in published PCT application WO 00/12041 to Stark et al., entitled "Orthoses for Joint Rehabilitation," and U.S. Pat. No. 6,689,056 to Kilcoyne et al., entitled "Implantable Monitoring Probe," both of which are incorporated herein by reference.

The smart implantable devices described herein provide a significant advance in treatment and monitoring capabilities. In addition, the communication capabilities provide for efficient management of the devices as well as suitable notification of health care professionals without the need for the patient to go to a health care facility. Thus, the devices provide improved care with increased efficiency to keep cost at a manageable level.

Patient Management Through a Central Server-Database

In general, the smart implant systems can be implemented in a basic format allowing for interfacing directly or indirectly with a health care professional in their office or other medical facility during a visit or stay. However, an implementation of the smart implant systems built upon an integrated communication system can achieve a much more effective and convenient system while possibly saving cost and achieving significantly improved patient results. In its full implementation, the system is built upon a central server or distributed servers with multiple layers of spokes extending from the server(s). The server(s) can interface with one or more databases, which can be distributed databases. Of course, in intermediate implementation's, layers of spokes and/or components of the interface can be eliminated while still achieving an effective system. While the systems described herein are directed to implantable devices, the centralized management can similarly be effective with non-implantable devices as well as hand held devices that interrogate the psychological and/or pain condition of a patient through a personal computer, which may or may not be ambulatory, in conjunction with another medical device or as a stand alone treatment device. Such psychological and/or pain interrogation of the patent can have broad applicability not only in the psychological treatment of the patient but also for facilitating treatment of the patient across a range of acute and chronic medical conditions, which almost invariably have a psychological component of the recovery process. Redundant hardware, software, database and/or server components may be part of the overall system in order to ensure system reliability.

The integrated communication system organization for interfacing with smart medical devices, whether implanted or not, is summarized in FIG. 1. FIG. 1 shows both a linear communication channel involving four linked components I, II, III and IV, as well as four layers of hubs and spokes 1, 2, 3, and 4 based off of the central server(s). The hub and spoke structure is discussed after a discussion of the linear linked components. Communications enabled medical devices 100 can be, for example, implantable, wearable and/or otherwise ambulatory with a patient. Medical device 100 can optionally comprise a processor 102 and/or sensors 104/treatment elements 106. Medical device 100 communicates along communications channel 108. Collectively, medical device 100, processor 102 and sensors 106/treatment elements 108 can be referred to as component I, to the extent the optional elements are present.

As shown in FIG. 1, communication channel 108 communicates with a patient communications hub 120. Patient communication hub 120 can interface with a patient computer 122, which can be an ambulatory computer such as a hand held computer, which can have a patient output channel 124, such as a screen or speaker to communicate with the patient. Collectively, patient communication hub 120, patient computer 122 and patient output channel 124 can be referred to as component II, to the extent that optional elements are present. Patient communication device 120 can further support entry of information through a keyboard, speaker or the like to communication information from the patient. The patient's communication hub further communicates through communications channel 126 with central server(s) 130.

Central server(s) 130 generally comprise communications elements 132, a computer system 134, a central database 136 with corresponding collected information 138, as well as algorithms and related software tools to perform a diagnosis and/or represent, evaluate, and/or modify or progress a patient's treatment protocol 138 or the like. Collectively, the central server(s) and its components can be referred to as component III, to the extent that optional components are present. Collected information within the database can comprise, for example, patient identification information, patient medical histories, medical literature, medical best practice data, institutional best practice data, patient specific data, diagnosis algorithms, treatment protocols, general treatment result summaries correlated with treatment protocols, device operating parameters, drug interaction data, and the like.

Algorithms and related software tools can comprise, for example, statistical analyses, simulation tools, workflow algorithms, and the like. Output from the central database can comprise updated patient protocol data streams that are transmitted to the smart stent or other instrumented implant. Outputs can also comprise tools to help clinicians with patient treatment including progress reports for inclusion in a patient medical record, visualization tools to monitor smart stent performance and simulation tools for protocol modeling, analysis and improvement.

The Central Server can also provide maintenance and administration facilities, comprised of interactive software tools, interfaces, and/or data entry facilities to help the clinician, authorized specialists within an entity that has licensed the system such as a hospital, or the engineers of a given device's manufacturer, to set up, test, modify, or delete clinical protocols or the parameter ranges and operating characteristics associated with a particular device being managed by the system. These tools can be implemented as a simple form that lists parameters and values, visual drag-and-drop tools that enable the clinical professional to select parameters from a list of parameters and drag the selected parameters into a visual representation of the treatment protocol, or as an application program interface that allows external software tools and programs to interact with the database.

Furthermore, the central server can monitor compliance and result evaluation related to the execution of self-diagnostic algorithms within the remote instrumented medical device, whether or not an implanted device. For example, at prescribed intervals, the central server can instruct and/or interrogate the remote medical device to initiate a self-diagnostic routine or request information regarding a previously executed routine. Records on the self diagnosis can be stored for future references. If an error condition is encountered, the central server can initiate an appropriate response, such as request that the patient notify their clinician, directly notifying the clinician, reprogram the device or other appropriate response.

The Central Server can also provide tools to help with the on-going operations and administration of the system, including security administration tools to manage the access and authority permissions of system users, firewall administration facilities, network performance monitoring facilities, interfaces to other systems within a medical institution or a manufacturer, server and database performance monitoring facilities, database administration facilities, system configuration management tools, tools to manage and update the software resident on the remote managed devices, back-up and recovery tools, as well as device logging and tracking facilities, including adverse event logging capabilities for government and manufacturer monitoring, and the like.

Central server(s) 130 further communicate through communications channel 140 to a clinician station 150. Clinician's station 150 can comprise a computer with an output channel to provide notification and/or to convey received information visually, audibly, in printed output, via email, via a wireless handheld device, such as Palm Corporation's Trio or Research in Motion's Blackberry device, via interactive video conference with the patient and possibly other local or remote members of the clinician team, or otherwise to the physician, clinician or other health care professional 152. Collectively, the clinician's station and associated components can be referred to a component IV, to the extent that optional components are present.

Components (I or II) and III of the system are optional in that one or the other or both of these components can be absent. FIG. 1 easily displays the resulting simpler systems by conceptually removing the missing component and connecting the in-line communication channels to close the resulting gap. Thus, if component II is absent, component I communicates directly with component III such that communication channels 108 and 126 merge, while if component I is absent, component II servers to provide patient input directly relating to pain or psychological condition of the patient. Similarly, if component III is absent, component II communicates directly with component IV, and communication channels 108 and 140 merge. If both components II and III are absent, component I communicates directly with component IV, and communication channels 108 and 140 merge. The remote communication of pain and psychological state of a patient to health care professionals is described further in copending U.S. patent application Ser. No. 10/997,737 to Stark et al., entitled "Remote Psychological Evaluation," incorporated herein by reference.

In some embodiments, the heart of the system is the central server(s) (component III) that coordinates communication in a multiple layered spoke structure. One layer of spokes (1) extends to a plurality of patients and corresponding components I and optionally II. The patients may or may not be equipped with the equivalent medical devices as each other, and similarly the patients may or may not be evaluated for similar types of medical conditions. Thus, the treatment of a large number of patients can be monitored and coordinated through one particular central database and associated server(s). A second layer of spokes (2) indicates connections with health care professionals represented through their corresponding communication channels by component IV. A large number of health care professionals may have access to the system, and these health care professionals may or may not be located at widely dispersed geographic locations. These health care professionals may be based in professional offices, or they may be located at hospitals, clinics or the like. If a particular patient is being treated by a plurality of health care professionals or clinicians, such as physicians with different specialties, the central database can provide easy access to the data to all attending health care professionals. To maintain appropriate privacy guarantees, appropriate password or other access control can be implemented to ensure that only appropriate information is dispensed to particular persons.

To facilitate administration of the health care system at reduced costs, the system can be designed such that information on treatment and results can be forwarded to payers, including, for example, government payers, such as Medicare and Medicaid, or private insurance providers and/or other health care administrators 160 from the central database server. Generally, access would be provided to a large number of administrative entities. This communication dimension corresponds with a third layer of spokes (3). This layer of communication spokes can improve efficiency and oversight while providing expected reimbursement of the healthcare professionals with efficient processing.

Furthermore, in some embodiments, the robustness of the system warrants system review. While individual health care professionals and possibly regulators 162 responsible for the overall care of a particular patient may have latitude to alter the treatment protocol for a particular patient, the range of protocols for a particular device, for example, as established by the manufacturer via engineering or clinical testing, as well as the treatment intervention function of the central database server itself, perhaps as established as clinical best practice by a health care provider that has licensed the system for internal use, generally cannot be changed in some embodiments. This practice ensures that most accepted treatment available to patients, which correlate with improved treatment results. To update and continuously improve the operation of the treatment protocols and accepted automated intervention by the central server, one or more selected professionals can have the responsibility for updating and improving the protocols and automated response of the server. These professionals interact with the server to evaluate protocols, ensure quality control and review best practices. This dimension of communication channels corresponds with a fourth layer of spokes (4).

An additional role of the central system can be to provide emergency notification of a received parameter outside of an acceptable range. The particular response can be selected based on the particular condition. In some circumstances, the patient can be notified through the patient interface of the patient's computer. The patient can be told a suitable response such as go to the doctor, take a certain drug, lie down, etc. In some circumstances, an ambulance or other emergency response vehicle can be called to go to the location of the patient, and the patient can also be notified in these circumstances if appropriate. In other circumstances, a clinician can be notified, although notification of a physician, nurse, technician or other health care professional can also be ancillary to other responses above.

General Implant Structure

Figure 2A:
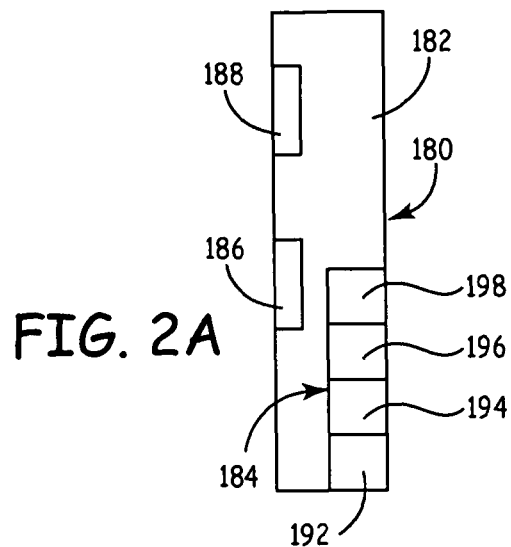
FIG. 2A is a schematic diagram of an implantable medical device.

A general smart implant is shown schematically in FIG. 2A. This implant can be a stent or other suitable medical implant, such as a drug or intervention delivery device implanted at or near an organ or other suitable location within a patient. Implant 180 can comprise, for example, one or more components, such as a frame or support structure 182, electronics 184, a sensor 186 and an output transducer 188. Electronics can comprise, for example, one or more of a power supply 192, a processor 194, memory 196 and a communication element 198, which can perform transmitting and/or receiving.

In some embodiments of particular interest, support structure 182 has structure corresponding to a stent. As noted above, a stent is a structure that can be inserted within a vessel without significantly blocking flow. Thus, in many embodiments, support structure 182 has a generally tubular structure. The stent generally can have a first low profile configuration for delivery and a second deployed configuration that contacts the vessel walls to stabilize the stent in the desired location. A wide range of stent designs are available. Representative stents are described, in U.S. Pat. No. 5,133,732 to Wiktor, entitled "Intravascular Stent," U.S. Pat. No. 5,135,536 to Hillstead, entitled "Endovascular Stent And Method," U.S. Pat. No. 5,843,120 to Israel et al., entitled "Flexible-Expandable Stent," U.S. Pat. No. 5,935,162 to Dang, entitled "Wire-Tubular Hybrid Stent," and U.S. Pat. No. 6,790,227 to Burgermeister, entitled "Flexible Stent," all of which are incorporated herein by reference. While some stent designs are self-expanding for deployment, others use a balloon or the like to impart expansion forces. Deployment with a balloon is described further in U.S. Pat. No. 6,610,069 to Euteneuer et al., entitled "Catheter Support for Stent Delivery," incorporated herein by reference.

The frames/support structure can be formed from a range of materials, such as metals, ceramics, polymers and a combination thereof. Suitable metals include, for example, a range of metals that have been used for medical applications, such as stainless steel, tantalum and various alloys, for example, shape memory alloys, spring metal alloys and/or Nitinol®, a nickel titanium alloy. As used herein, metal refers to metal elements in a metallic form, generally substantially unoxidized. Metal may be selected based on mechanical and/or electromagnetic properties. Suitable polymers include, for example, elastomers and plastics, such as polyethylene, polypropylene, polyurethanes, polyesters, and the like. The stents can be formed partially or completely from a bioresporbable polymer, such as those known in the art, for example, homopolymers or copolymers of lactic acid, glycolic acid and acetic acid. More complex stents may have a substructure with elements, such as wire, laminations, voids, mechanical elements, and/or electronic or magnetic active or passive elements. The materials can be processed, for example, using conventional techniques, such as extrusion, molding, machining, calendering, and combinations thereof. The structure may be configured effectuate particular selected functions of the devices, as described in detail herein.

In general, most stent designs can be adapted for use as a support structure for an impantable device as described herein. For example, the other components can be mounted on one of these stent designs, for example, along the length of the stent at one edge. Thus, the remaining circumference of the stent is the expandable material. If a reasonable fraction of the stent circumference is not expanding, the stent generally still has proper expansion upon deployment. However, since stents described herein may or may not provide a function related to the enhancing or maintenance of flow through the vessel, the mechanical performance characteristics of a smart stent may be less or more demanding than for some conventional stents, depending on the particular embodiment.

Prosthetic vessels, which can be implanted as vascular grafts or the like, may or may not have a more rigid frame. However, with respect to the general implant structure, the entire prosthetic vessel can be considered support structure 182 with the remaining functional components suitably attached to the support structure. In generally, the walls of the vessel can be synthetic materials, tissue materials or combinations thereof. Suitable synthetic materials include, for example, suitable woven polymers, such as Dacron® polyester or the like. Vascular grafts formed with polyethylene terephthalate (PET) polyester with a polyurethane coating is described further, for example, in U.S. Pat. No. 6,939,377 to Jayaraman et al., entitled "coated Vascular Grafts And Methods Of Use," incorporated herein by reference. Suitable tissue can be decellularized tissue or relatively intact tissue. Tissue is often crosslinked, for example, with glutaraldehyde or other suitable biocompatible crosslinking agent, to provide a non-allergenic material with suitable mechanical strength. Suitable tissue for forming prosthetic vessels is described further, for example, in U.S. Pat. No. 6,471,723 to Ashworth et al., entitled "Biocompatible Prosthetic Tissue," incorporated herein by reference.

Figure 2B:
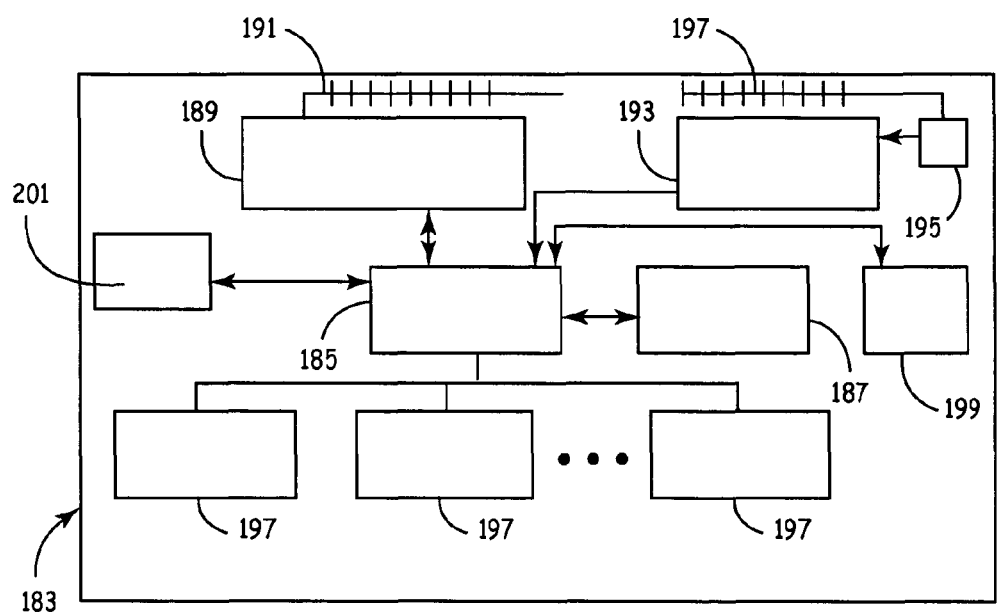
FIG. 2B is a schematic diagram of the electronics module and other electrical components suitable for use with an implantable medical device.

A schematic diagram of the interconnections of electrical components within a smart stent or other smart implantable device is shown in FIG. 2B. These devices can be placed within a single platform or housing, split between a plurality of platforms or housings, or directly mounted on a device or set of devices at suitable locations and with suitable connections. Referring to FIG. 2B, electronic architecture 183 comprises a central processor 185 operably connected to a memory device 187, which can be volatile and/or non-volatile memory, transmitter/receiver 189 with antenna 191 and power supply/battery 193, which can be connected to a charge device 195 and optional antenna 197 to received external recharging. Furthermore, processor 185 can be connected optionally to various transducers, such as one or more measurement/input transducers 197, a drug delivery device 199, which can comprise a MEMS transducer or the like, and/or other output transducers 201, such as a contact device to vibrate a vessel.

For metal stents or partly metal stents, the entire stent or a significant portion thereof can function as an induction coil for receiving an RF signal. Polymer can be used to provide structural features and appropriate electrical insulation. Thus, the stent can function as an antenna. The stent as an antenna can be electrically connected to suitable transmitter and/or receiver. In addition, the electromagnetic interaction with a metal coil stent can be used to direct an electric current in association with the stent. This can be used, for example, to recharge a battery or to direct a current into tissue or to directly power a device, such as a pacing device, defibrillation device or other implantable device. The field applied to the coil can be a static field or an oscillating field, such as an RF field. A magnetic field can be applied with the magnets of an MRI instrument to induce a current. In some embodiments, an electrical current can be used to stimulate drug release either through a MEMS effect or by initiating the biodegradation of a polymer. Similarly, such coil structures or the like can be implanted within or on a prosthetic vessel to provide comparable functions.

Figure 3:
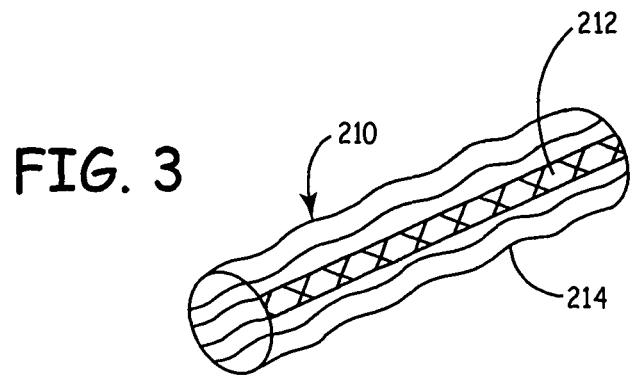
FIG. 3 is a schematic perspective view of a first embodiment of a smart implantable stent.

One representative stent embodiment is shown schematically in FIG. 3. In this embodiment, smart stent 210 comprises a functional carriage 212 and an expandable mesh 214. Expandable mesh 214 can take any convenient form such as known stent mesh forms. Functional carriage 212 can support electronics 184, sensors 186 and/or functional transducers 188. Functional elements can be divided among a plurality of carriages or the like. Also, a carriage may or may not extend over the entire length of the stent.

Figure 4:
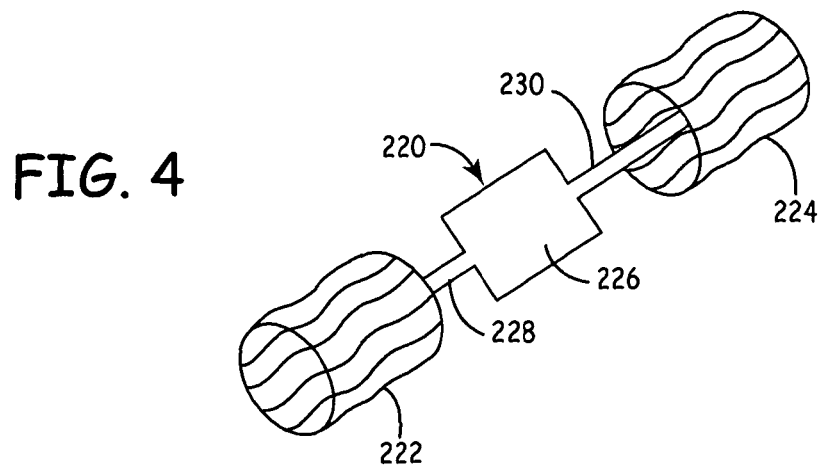
FIG. 4 is a schematic perspective view of a second embodiment of a smart implantable stent.

An alternative representative stent embodiment is shown in FIG. 4. Smart stent 220 comprises a first expandable segment 222, a second expandable segment 224 and a functional carriage 226. Expandable segments 222 and 224 can have structures corresponding, for example, to existing stent structures or newly developed stent structures, which may or may not be self-expanding. Carriage 226 is attached to first expandable segment 222 with bridge 228, and carriage 226 is attached to second expandable segment 224 with bridge 230. Additional carriages can be attached to the structure. Carriage can comprise, for example, electronics, sensors and/or functional transducers.

A further alternative stent embodiment is shown in FIG. 5. In this embodiment, stent 240 comprises an expandable support structure 242 and a transducer 244. Expandable support structure 242 can be adapted from a conventional stent design. Transducer 244 can be a MEMS device or other transducer. Transducer has a suitable electrical connection 246. Electrical connection 246 connects to a wire 248 that is connected to a controller 250. Controller 250 can have a processor, transmitter, receiver, power supply and other suitable electrical components. Upon deployment, rigid electrical connection 246 can pierce the vessel. Then, wire 248 can be surgically connected, and controller surgically implanted.

An alternative stent embodiment with a fundamentally different structure is shown in FIG. 6. Smart stent 260 may not be designed generally to facilitate the opening of a vessel with respect to its flow. Smart stent 260 is directed to a device that is designed for measurement or treatment delivery. As such, smart stent 260 only covers a fraction of the vessel's circumference. Smart stent 260 comprises at least one transducer 262, which can be a treatment transducer or a measurement transducer, and electronics 264. Electronics 264 can comprise one or more convenient electronic components discussed above. Smart stent 260 is anchored within the vessel. A shown in FIG. 6, four barbed anchors 266 are shown. These anchors can be supplemented with a surgical adhesive or the like. Different numbers of anchors, different placement of anchors and different anchor designs can be used as desired.

While four representative stent structures are shown in FIGS. 3-6, features of these stents can be combined as desired. In addition, other smart stent designs can be adapted based on these structures in the spirit of the various stent designs and particular features of the figures. Also, these stents can incorporate radiopaque markers to enable visualization of the smart stent following deployment. Suitable radiopaque materials include, for example, radiopaque polymers, metals, such as platinum-iridium or platinum-tungsten, and metal compositions in polymers, such as radio-pacifiers, for example, barium sulfate, bismuth trioxide, bismuth subcarbonate, powdered tungsten, powdered tantalum or the like. Radiopaque polymers include, for example, iodinated and brominated polymers, as described in U.S. Pat. No. 6,475,477 to Kohn et al., entitled "Radio-Opaque Polymer Biomaterials," incorporated herein by reference.

Figure 7:
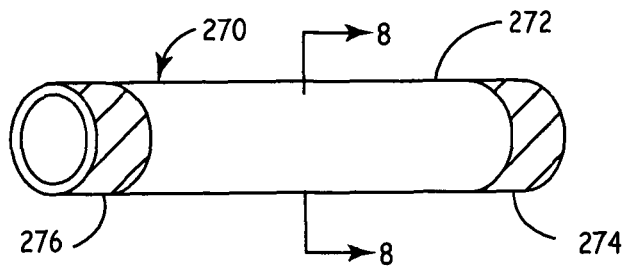
FIG. 7 is a side perspective view of a prosthetic vessel.

A representative prosthetic vessel is shown in FIG. 7. Prosthetic vessel 270 comprises a generally tubular graft 272 and optional sewing cuffs 274, 276. Sewing cuffs 274, 276 can be formed from fabric or the like to facilitate suturing or otherwise fastening the vessel to a native vessel. Instrumentation described herein is generally positioned such that a component is in contact with the interior flow of the vessel, although in some embodiments, the instrumentation can be isolated from the interior surface of the prosthetic vessel. Various representative embodiments are shown in sectional views 8A-8E.

Figure 8A:
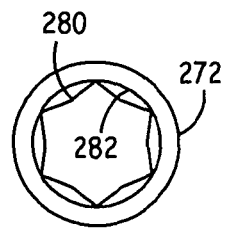
FIG. 8A is a sectional view of a first embodiment of an instrumented prosthetic vessel with the section taken along line 8-8 of FIG. 7.
Figure 8B:
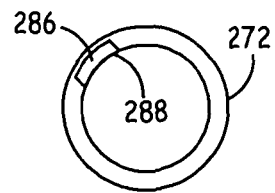
FIG. 8B is a sectional view of another embodiment of an instrumented prosthetic vessel with the section taken along line 8-8 of FIG. 7.
Figure 8C:
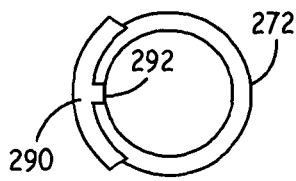
FIG. 8C is a sectional view of a further embodiment of an instrumented prosthetic vessel with the section taken along line 8-8 of FIG. 7.
Figure 8D:
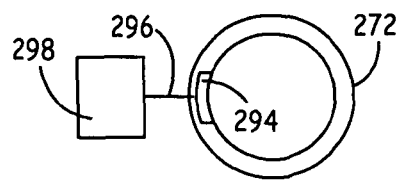
FIG. 8D is a sectional view of an additional embodiment of an instrumented prosthetic vessel with the section taken along line 8-8 of FIG. 7.
Figure 8E:
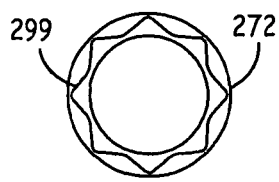
FIG. 8E is a sectional view of yet another embodiment of an instrumented prosthetic vessel with the section taken along line 8-8 of FIG. 7.

Referring to a first representative embodiment of a prosthetic vessel in FIG. 8A, instrumentalities are mounted on a support structure 280 contacting the inner surface 282 of tubular element 272. Support structure 280 can be similar to a conventional stent structure, although a wide range of structures are suitable for support structure 280 since it can be sutured or otherwise fastened to tubular element 272. Referring to FIG. 8B, instrumentalities 286, such as a transducer and/or other electronics, are embedded within the wall of tubular element 272, with a transducer surface 288 exposed to the interior flow through the vessel. Referring to another alternative smart prosthetic vessel embodiment in FIG. 8C, instrumentalities 290 are mounted on the side of tubular element 272 with a transducer surface 292 penetrating to the interior surface of tubular element 272. A further alternative embodiment of a smart prosthetic vessel is depicted in FIG. 8D in which transducer 294 is mounted with exposure to the inner surface of tubular element 272 and with a wired or wireless electrical connection 296 with electronics 298. Electronics 298 may or may not be supported by tubular element 272. Referring to an alternative embodiment of a smart prosthetic vessel in FIG. 8E, instrumentalities 299 are completely embedded within tubular element 272.

For use with implantable devices, physical constraints on the systems provide performance guidelines for the electronics used to control the device. Suitable power supplies may or may not be based on delivery of power from outside of the patient. With respect to the power consumption if batteries are used, very thin batteries can be formed, as described further in published PCT application WO 01/35473A to Buckley et al., entitled "Electrodes Including Particles of Specific Sizes," incorporated herein by reference. These thin batteries can extend over a significant fraction of the device surface to extend the capacity of the battery. Also, if battery storage is used, the battery can be recharged using an RF signal to supply power to the device. See, for example, U.S. Pat. No. 6,166,518 to Guillermo et al., entitled "Implantable Power Management System," and Published U.S. Application 2004/0106963A to Tsukamoto et al., entitled "Implantable Medical Power Module," both of which are incorporated herein by reference.

Processors with corresponding memory can be adapted for these uses. In general, the processors/controllers can have considerably less performance capabilities than readily available hand held computers since they can download information external to the patient for more sophisticated processing. Suitable miniature processors and memory can be formed. U.S. Pat. No. 6,140,697 to Usami et al., entitled "Semiconductor Devices," incorporated herein by reference, describes integrated circuits with a thickness on the order of 250 microns. Commercial microprocessors include, for example, ARM7 processors (from ARM Limited) with areas as small as 0.26 square millimeters. For both the controller for the implanted device and for the hand held controller described below, security codes can be used to restrict instructions from unauthorized sources that can alter the performance of the devices in an inappropriate way.

With respect to communication elements, small radio frequency antennas can be used, or in some embodiments the antenna function can be the primary function of the device. Suitable antenna are described, for example, in U.S. Pat. No. 6,563,464 to Ballantine et al., entitled "Integrated On-chip Half-Wave Dipole Antenna Structure," and U.S. Pat. No. 6,718,163 to Tandy, entitled "Method of Operating Microelectronic Devices, and Methods of Providing Microelectronic Devices," both of which are incorporated herein by reference. Antenna with sub-millimeter dimensions can be formed. These devices can involve very small structures with suitable antenna. Currently, the Federal Communication Commission has set aside a frequency band between 402 and 405 MHz specifically for wireless communication between implanted medical devices and external equipment. Based on the description above, the RF antenna can be incorporated on the chip with the processor and the battery can be integrated into a device with the chip.

Suitable sensors and the like are described further in published PCT application WO 00/12041 to Stark et al., entitled "Orthoses for Joint Rehabilitation," and U.S. Pat. No. 6,689,056 to Kilcoyne et al., entitled "Implantable Monitoring Probe," both of which are incorporated herein by reference. Suitable MEMS devices, which can be adapted as sensors or as output transducers, are described below and can be adapted for other mechanical applications within the implantable devices. In general, sensors comprise transducers that reduce a physical signal associated with the sensor into an analog, a digital or other electrical signal suitable for further processing. The electrical signal can be transmitted from the body to an external receiver, for example, using wireless communication. In some representative embodiments of interest, the signals are stored for transmission at a later time, although the signals can be transmitted intermittently without any prompting. In general, the implanted device may have a microprocessor, an appropriate power source and appropriate memory to mediate the interface between the transmitter and the sensor.

Furthermore, output transducers can be associated with the medical device implant in addition to or as an alternative to measurement transducers. An output transducer propagates energy in response to an electrical signal, which correspondingly may be generated in response to a biological condition, a radio transmission and electromagnetic signal or other biological or physical condition. The output transducers can be energy propagating transducers. Suitable energy propagating transducers can be RF transmitters, heaters, and/or electrodes that apply, receive or transduce a constant or pulsed current over a selected time frame. Electric currents, heat and/or other biological stresses that may stimulate healing or other biological activity, such as synthesis of biological compositions, secretion of compositions and/or generation of biological electrical impulses. Energy propagating transducers are described further for external orthopedic devices, which can be adapted for implantable based on the teachings herein, in published PCT application WO 96/36278 to Stark, entitled "An Orthopedic Device Supporting Two Or More Treatment Systems and Associated methods," incorporated herein by reference.

Similarly, drug delivery can be associated with a medical implant. Suitable drugs include, for example, a metabolically active agent, as steroids, endocrine or pain medication, bone growth hormones, insulin, cellular cytokines and the like and combinations thereof. Suitable drug delivery systems are described in the following. Separate drug delivery units can be selectively used to deliver a particular drug based on a sensed desire for the particular drug or based on external instructions. Drug delivery can be initiated automatically, by the physician via remote controls or by the patient.

External Controller

In general, an external controller coordinates collection of data from the implant, the communication method of the implant, communication of instructions to the implant and communication between the instrument and health care professionals and may comprise an appropriate amplifier for signals received from an implantable device. A standard microcomputer or workstation with an appropriate processor/microprocessor can be adapted for use as an external communicator through the connection of an appropriate transmitter and/or receiver to the computer through a suitable port. In some embodiments, the external coordination instrument comprises an ambulatory communicating and/or computing device, such as a personal digital assistant, for example, a Trio™ or other similar commercial devices, adapted for this use or a specially designed hand held device.

A suitable device is shown schematically in FIG. 9. External controller 300 comprises a case 302, a display 304, a keyboard 306, additional optional switches 308 and one or more optional ports 310, such as USB, ethernet, a power supply port and other suitable ports. A schematic depiction of the interior of the device is shown in the insert of FIG. 9. As shown in the insert, controller 300 comprises a power supply 316, a processor 318, additional memory 320, a receiver 322, a transmitter 324 and suitable buses 326 to interconnect the components.

A separate antenna can be attached if desired to facilitate receiving and/or transmitting a weak signal from an implanted device. Some possible additional features of the device is described further in published PCT application WO 00/12041 to Stark et al., entitled "Orthoses for Joint Rehabilitation," incorporated herein by reference. Use of sensors with external orthopedic devices is described further in published PCT application WO 00/12041 to Stark et al., entitled "Orthoses for Joint Rehabilitation," and in U.S. Pat. No. 6,540,707 to Stark et al., entitled "Orthoses," both of which are incorporated herein by reference. These sensors and associated electronics can be adapted for use within implants based on the description herein. Energy propagating transducers are described further for external orthopedic devices, which can be adapted for implantable based on the teachings herein, in published PCT application WO 96/36278 to Stark, entitled "An Orthopedic Device Supporting Two Or More Treatment Systems and Associated methods," incorporated herein by reference.

In general, controller of the implanted medical device and/or the hand held controller of FIG. 9 can be remotely monitored and or reprogrammed. In general, the hand held controller and/or a laptop and/or table top computer can be used to network the system for communication with a remote healthcare professional, such as a physician, and/or with a central monitoring station with a central database, which can be useful for remote reprogramming and/or self-adjustment via data collection and application of appropriate algorithms. The network can be a dedicated network/communication channel, the internet/world-wide-web, other existing networks or a yet to be developed network. Communication can be through satellite, wifi, microwave transmission, radio transmission, acoustic, phone lines, optical fiber, other electrical wire, a combination thereof or the like. Suitable control and communication protocols for medical devices, their networking and database manipulations are described further in the patents and applications described above and incorporated herein by reference. For both the controller for the implanted device and for the hand held controller of FIG. 3, security codes can be used to restrict instructions from unauthorized sources that can alter the performance of the devices in an inappropriate way.

Drug Delivery Systems and MEMS Applications

As described above, stents and other implantable medical devices are suitable for the delivery of drugs, other compounds and the like. Microelectromechanical (MEMS) devices are particularly suited for control of the delivery of bioactive agents, such as drugs, within small devices. MEMS devices within small implantable medical devices can also be used for the performance of measurements and/or for the delivery of other treatments. MEMS devices can be considered transducers within the context of the general figures above relating to smart implantable stent structures. Other release systems for bioactive agents can be directly controlled through the application of an electric field, as described further below.

An implantable medical device capable of controlled drug delivery is shown schematically in FIG. 10. Implantable device 340 comprises a support structure 342, a reservoir of a bioactive agent 344, a cover 346 that blocks an opening 348 into reservoir 344 in a closed configuration, a MEMS device 350 that is operably connected to cover 346 and an electronics module 352 operably connected to MEMS device 350. Support structure 342 can be a stent frame or other convenient implantable structure. Reservoir 344 can hold a bioactive agent, such as a drug, in a suitable form for delivery into a patient. The bioactive agent can be in a form that slowly dissolves into the blood stream upon contact, a composition with a sufficient viscosity such that the composition diffuses slowly from the reservoir, or other suitable form for controlled delivery. Cover 346 can be made from a suitable material, such as a metal, an elastomer polymer, a ceramic or a combination thereof. The MEMS device is constructed to open and close the cover to allow for disbursal of the bioactive agent. The electronics module can be based on the electronics components described above.

Suitable drugs/bioactive agents include, for example, antimicrobial agents, hormones, cytokines, growth factors, hormone releasing factors, transcription factors, infectious agents or vectors, antithrombogenic agents, anti-restenosis agents, calcium channel blockers, antirestenosis agents, such as pacitaxel and sirolimus, blood pressure reducing agents, ionic forms thereof, combinations thereof and the like. Many of these drugs are protein based, and other protein based drugs can be used as well as the nucleic acids coding for these drugs. Formulations for controlled delivery are well known in the art. Biological formulations generally comprise fillers, conditioners, diluents, controlled release agents, carriers and the like, which may be well known in the art. Further discussion of bioactive agent/drug formulations is found, for example, in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol. 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol. 40 (Gilbert S. Banker, Christopher T. Rhodes, Eds.), incorporated by reference for their teachings on suitable formulations of bioactive agents.

The MEMS device can be programmed, for example, using Aspect Oriented Programming, Object Oriented Programming or other industry standard techniques to open the cover to expose a drug or release the agent chemically or physically within the reservoir to the surrounding fluid for controlled delivery of the drug/therapeutic agent. An acoustically actuated MEMS device suitable for this application is described further in published U.S. patent application 2002/0017834A to MacDonald, entitled "Acoustically Actuated MEMS Devices," incorporated herein by reference. Similarly, a MEMS based pump element can be used. Suitable MEMS pumps are described in U.S. Pat. No. 6,531,417 to Choi et al., entitled "Thermally Driven Micro-Pump Buried In A silicon Substrate and method For Fabricating the Same," and published U.S. Patent Application 2004/0073175 to Jacobson et al., entitled "Infusion System," both of which are incorporated herein by reference. These systems can be used to open and close the drug reservoir, or prepare or release the bioactive agent, or provide a substrate or sink for collecting bodily chemicals, therapeutic agents or toxins.

For placement in a blood vessel or other vessel within the patient, the stent structures described above with respect to FIGS. 2-6 can be adapted to incorporate a MEMS device described herein. The MEMS devices are described above and can be adapted for other mechanical applications within the implantable devices. For example, a MEMS structure can be used to dislodge thrombus built up on or in the stent for removal in a thrombectomy procedure.

Electric fields can be used directly for drug delivery release from micro-reservoirs covered with appropriate electrically responsive materials. The reservoirs can be formed using microfabrication techniques, such as photolithography and other conventional techniques. A matrix for the bioactive agent in the reservoir can comprise a polymer. Suitable biodegradable polymers include, for example, polyamides, poly (amino acids), poly(peptides), polyesters, copolymers thereof, and mixtures thereof. Suitable non-degradable polymers include, for example, polyethers, polyacrylates, polymethacrylates, polyurethanes, cellulose, derivatives thereof, copolymers thereof and mixtures thereof. Suitable cap materials can dissolve upon application of a current. Suitable materials include, for example, gold, silver, zinc and erodable polymer gels. Suitable release systems from micro-reservoirs adaptable for stents are described further, for example, in U.S. Pat. No. 6,875,208B to Santini Jr., et al., entitled, "Microchip Devices With Improved Reservoir Opening," U.S. Pat. No. 6,123,861 to Santini Jr., et al., entitled Fabrication of Microchip Drug Delivery Devices," and U.S. Pat. No. 6,858,220B to Greenberg et al., entitled Implantable Microfluidic Delivery System Using Ultra-Nanocrystalline Diamond Coating," all three of which are incorporated herein by reference. A stent structure can comprise a plurality of reservoirs, such as two, five, ten or more, with comparable caps such that the release of the individual reservoirs can be controlled individually as desired.

Smart Stent and Prosthetic Vessel Structures

Some specific stent structures of interest are described further in this section. Stents described herein include, for example, stents that facilitate occlusion sensing, stents that perform electromagnetic treatment, multiple layered stents, stents with controlled drug delivery and stents suitable for detecting aneurysms. While several of these stent embodiments make use of the smart stent technology described herein, some embodiment of the stents make use of external measurements or are non-instrumented embodiments. In general, each of these stent structures can be adapted for incorporation into a corresponding smart prosthetic vessel. Specifically, transducers associated with the specific embodiments can be incorporated into prosthetic vessels in the configurations shown in FIGS. 8A-8E.

With respect to measurement capability, several stent embodiments for measurements related to occlusion are shown schematically in FIGS. 11-22 for several different measurement approaches. These approaches can be specifically directed to evaluate plaque or other thrombus build up or to detect aneurysms. Plaque and thrombus are used generally to refer to any material built up within the vessel regardless of the composition of the material. These different sensor designs use a range of different physics-based techniques to sense vessel blockage, build up and/or aneurysms.

Referring to FIGS. 11A and 11B, a first embodiment of a stent is shown that is suitable for occlusion sensing. Stent 360 comprises a material that is easy to detect through ultrasound. The acoustic impedance changes as plaque 362 builds up within the blood vessel 364 indicating restenosis at the stent. Stent 360 comprises a plurality of acoustic reflectors 366. Suitable acoustic reflectors 366 can be, for example, air-filled spheres embedded in the wall of the stent. In FIG. 11B, an ultrasonic transducer 368 is shown reflecting off of points 1 and 2 corresponding to two reflectors 366 of stent 360. The acoustic response of point 1 relative to point 2 changes as plaque accumulates in the vessel.

Figure 12A:
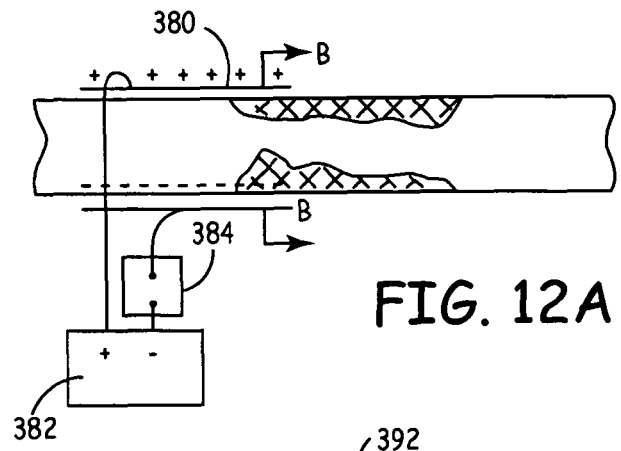
FIG. 12A is a schematic sectional side view of a stent deployed in a blood vessel in which the stent is configured to make measurements of capacitance with the section taken through the center of the vessel.
Figure 12B:
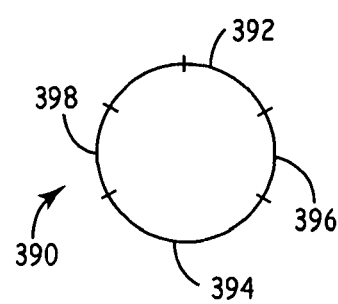
FIG. 12B is a sectional end view of the stent of FIG. 12A with the section taken along line B-B of FIG. 12A.

Another embodiment is shown in FIGS. 12A and 12B. The principle of this embodiment is shown schematically in FIG. 12A. Referring to FIG. 12A, stent 380 is used to generate an electric field across the vessel and between two plates. The field can be generated with ac current, such as an RF frequency or with direct current. The capacitance and/or electrical impedance can be measured to determine the presence of plaque build up. A power source 382 and switch 384, such as an rf switch and/or an on/off switch, are depicted schematically connected to stent 380. Referring to FIG. 12B, an end view is shown of an embodiment of a stent to implement the schematic arrangement in FIG. 12A. Stent 390 comprises a first plate 392, a second plate 394 and electrically insulating sections 396, 398. A controller/electronics can be structurally connected to the other stent components using any of the arrangement in FIGS. 3-5 or two components as shown in FIG. 6 where a controller is electrically connected to the two components.

Figure 13:
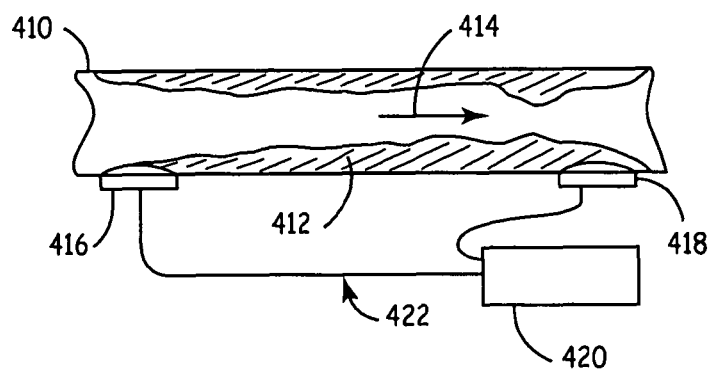
FIG. 13 is a schematic depiction of two pressure sensors mounted within a stent and deployed in a blood vessel with one sensor being deployed downstream from the other sensor.

An embodiment designed to measure pressure changes within a vessel is shown in FIG. 13. As shown in FIG. 13, blood vessel 410 has plaque build up 412. Flow within the vessel is indicated with flow arrow 414. As shown in FIG. 11, two pressure sensors 416, 418 are placed in vessel 410 with sensor 416 being upstream from sensor 418. Values from the pressure sensors 416, 418 can be compared with comparator 420. Comparator 420 can be external to the patient in wireless communication with pressure sensors 416, 418, or comparator 420 can be implanted. If comparator 420 is implanted, it can be physically associated with a structure at one of the pressure sensors with wired or wireless communication channels 422 between the spaced apart sensor and the communicator. If the communicator is implanted and not directly physically associated with structures housing the pressure sensors, wired or wireless communication can connect the sensors with the comparator. While two pressure sensors are shown in FIG. 13, more than two pressure sensors can be used if desired, such as three, four or more pressure sensors. The pressure sensors can be mounted on stent supports, such as the structures shown in FIGS. 2-6. The comparator can be based on electronics such as that described above, or the comparator can be a function or algorithm calculated real time in a microprocessor located adjacent to the stent. Pressure differentials between the two or more sensors can be indicative of a pressure drop associated with plaque deposits. Specifically, a downstream pressure drop can be indicative of constriction between the two sensors.

Figure 14A:
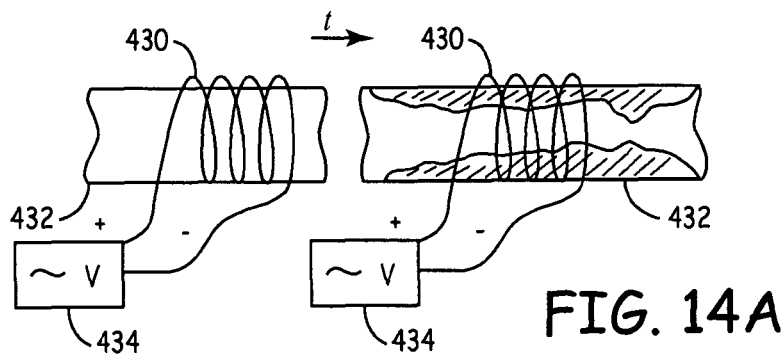
FIG. 14A is a schematic side view of a stent forming an induction coil within a blood vessel with the right view representing a later time relative to the left view.
Figure 14B:
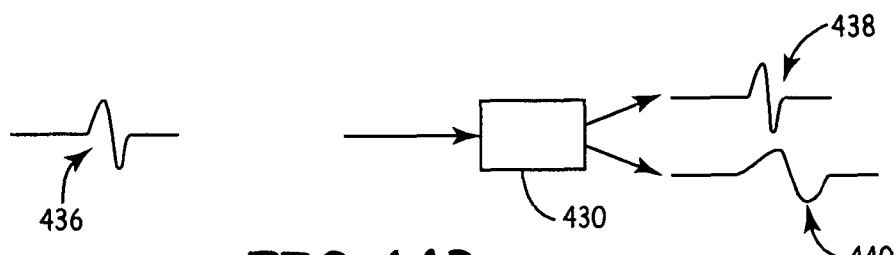
FIG. 14B depicted the application of a magnetic pulse to the induction coil which induces different current signals depending on the presence (lower plot of current response) or absence (upper plot of current response) of plaque.

A system that is based on changes over time is depicted in FIG. 14A. An electrically conductive induction coil 430 is placed within vessel 432. The induction coil is connected to a voltage device 434, such as a voltmeter. The coil and voltmeter can be incorporated, for example, into one of the stent structures depicted above in FIGS. 2-6. The left view in FIG. 14A shows the vessel at a first point in time, while the right view shows the vessel following the passage of time (t) over which plaque has built up in the vessel. Referring to FIG. 14B, the left view schematically depicts the application of a magnetic pulse 436 external to the patient. This magnetic pulse 436 stimulates current in induction coil 430 in the blood vessel. The magnitude of the electrical inductance resulting from the magnetic pulse is a function of the plaque build up as indicated schematically in the two different current signals 438, 440 on the right of FIG. 14B due to a change in the material properties within the interior of the coil. Alternatively, voltage device 434 can be a voltage generator of an AC, DC or transient signal that periodically generates a signal. The measured coil impedance or impulse response after application of current from the voltage generator is then a function of the plaque volume. Voltage generator 434 can be triggered externally to poll the device or can be under microprocessor control.

Figure 15:
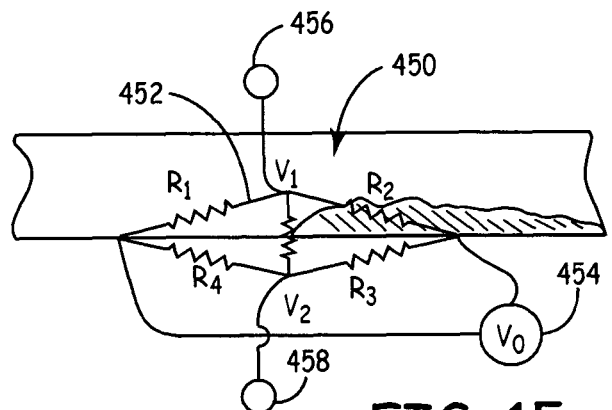
FIG. 15 is a schematic depiction of a stent-based measurement system deployed in a blood vessel with electrically resistive elements that are configured as a Wheatstone bridge such that plaque build up alters the electrical resistance of some elements to unbalance the bridge.

A stent for detecting plaque from changes at different positions in the vessel is shown in FIG. 15. In this embodiment, stent 450 comprises a Wheatstone bridge 452. A Wheatstone bridge comprises five electrical resistors connected to a voltage supply 454. Other resistance bridges are known in the art and can be substituted for the Wheatstone bridge. The electrical resistance will be a function of plaque build up. Voltmeters 456, 458 are used to measure the voltage at points $V_1$ and $V_2$. If the voltage values from voltmeters 456, 458 are equal, then the resistances are balanced across the bridge and there is no plaque on the side of the bridge inside the vessel. A resistive imbalance indicates plaque build up. This is due to a change in the electrical resistance due to the association of the plaque with the resistor. Each resistor can be formed from resistive wire in contact with the interior of the vessel such that the surface coating (for example, plaque build-up) can alter the electrical conductivity.

If, as shown schematically in FIG. 15, one side of the bridge is associated with plaque but the other side is associated with a significantly different amount of plaque or no plaque, the voltage measurements from voltmeters 456, 458 are different. Changes of the bridge balance over time may be further indicative of plaque build up or the like. The components can be assembled into the stent structures described above with respect to FIGS. 2-6. Specifically, the entire bridge can be assembled into a single stent with appropriate conductive and electrically insulating components. Alternatively, each side of the bridge can be assembled into a stent, which are placed in a spaced apart configuration, and appropriate electrical connections connect the two sides of the bridge. Similarly, a number of separate components can be placed into the vessel to form the bridge, where each component may or may not be associated with a stent structure. Thus, there are a number of suitable configurations for forming the bridge within the vessel.

Figure 16:
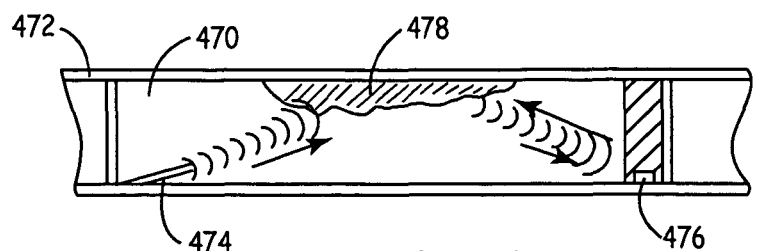
FIG. 16 is a sectional side view of an acoustic transmitter/receiver embodied within a stent and deployed within a blood vessel along with an acoustic reflector such that the acoustic properties in the blood vessel can be measured with the section taken through the center of the vessel.
Figure 17:
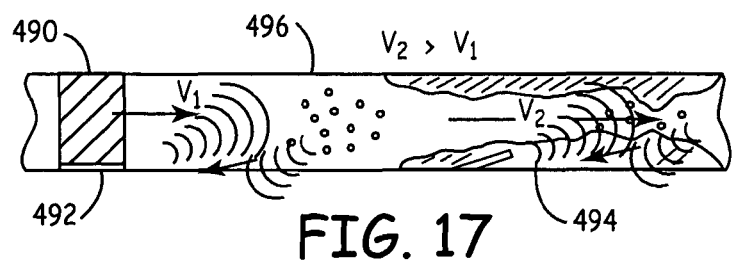
FIG. 17 is a sectional side view of an acoustic sensor within a stent and deployed within a blood vessel configured to measure Doppler shifts of acoustic waves within the blood vessel with the section taken through the center of the vessel.

Stent embodiments are shown in FIGS. 16 and 17 for plaque detection based on acoustic properties within a blood vessel. Referring to FIG. 16, stent 470 is located within vessel 472. Stent 470 comprises an acoustic emitter and detector 474. Similarly, the emitter and detector can be separated. Piezoelectric materials and/or electroactive polymers can be used to form the acoustic transducers. Acoustic transducers formed with piezoelectric films are described further in U.S. Pat. No. 6,937,736 to Toda, entitled "Acoustic Sensor Using Curved Piezoelectric Film," incorporated herein by reference. Acoustic sensors formed with electroactive polymers are described further in U.S. Pat. No. 6,781,284 to Pelrine et al., entitled "Electroactive Polymer Transducers and Actuators," incorporated herein by reference. Stent 470 also comprises an acoustic reflective element 476. Reflective element 476 can include one or more air filled bladders, hollow polymer balls, bladders filled with another fluid with sufficiently different properties than blood or the like or combinations thereof. Acoustic waves will reflect back differently depending on whether or not plaque 478 is present in vessel 472. In addition, the measurements can be monitored for changes in the measurements over time, which may be indicative of plaque build up or the like. Suitable electronics can be used to analyze the signal. Smart stent structures in FIGS. 2-6 can be adapted for these uses.

Referring to FIG. 17, stent 490 comprises an acoustic emitter and detector 492, although there can be a plurality of emitters and/or detectors along the length of the stent. Emitted sound waves are reflected off of blood cells and are Doppler shifted due to the blood flow velocity. If an occlusion 494 is present as a result of plaque or the like in vessel 496, blood flows faster through the occluded region resulting in a greater degree of Doppler shifting from the portion of the signal reflected from that portion of the vessel. The received acoustic wave at acoustic receiver 492 can be analyzed with respect to Doppler shift to detect the presence or absence of plaque. These Doppler shifts can be monitored over time to detect changes in the Doppler shift that would be indicative of plaque build up or the like. Suitable time periods can be selected to be reasonable under the particular circumstances.

Figure 18A:
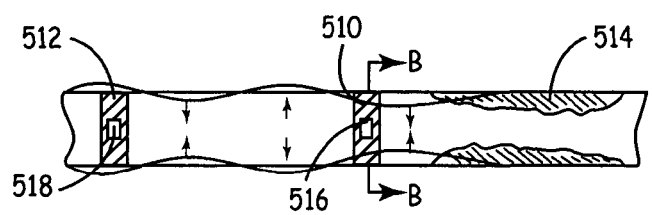
FIG. 18A is a schematic side view of transducers deployed in a stent that is deployed within a blood vessel to induce vibration of the vessel and measure the vibrational response of the vessel in which the section is taken through the center of the vessel.
Figure 18B:
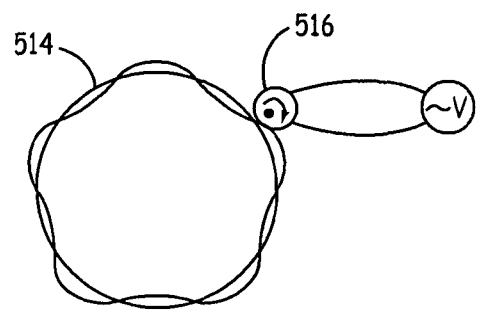
FIG. 18B is a schematic sectional end view depicting a transducer contacting the stent in a configuration to induce vibrations of the blood vessel with the section taken along line B-B of FIG. 18A.

An embodiment in FIGS. 18A and 18B, detects the vibrations transmitted through the vessel wall. Stent 510 and stent 512 are placed within vessel 514. Stent 510 comprises a contact plate 516, which can be a MEMS structure or other suitable transducer. Stent 512 comprises an acoustic receiver 518 that receives vibrations transmitted along the vessel due to vibration of the vessel by the contact plate. Acoustic receiver 518 can be formed from piezoelectric material, from an accelerometer or from other suitable materials such as the materials described above for use in acoustic transducers. The signal received by acoustic receiver 518 can be Fourier transformed to yield the vibrational spectrum that is diagnostic of the mechanical properties of the vessel including, for example, the presence or absence of plaque. A clear vessel resonates with a resonance frequency that changes in frequency if plaque is present. Furthermore, changes can be monitored over time to measure changes that can be indicative of the build up of plaque or the like. Again, the smart stents of FIGS. 2-6 can be adapted for these stents.

Figure 19A:
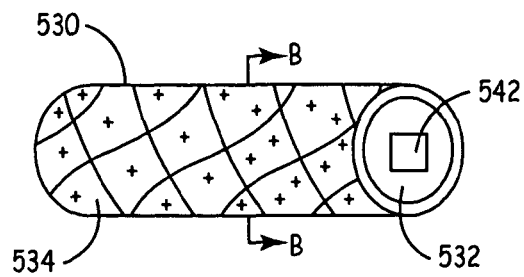
FIG. 19A is a schematic perspective view of a stent configured to induce a positive surface charge on the surface of the stent.
Figure 19B:
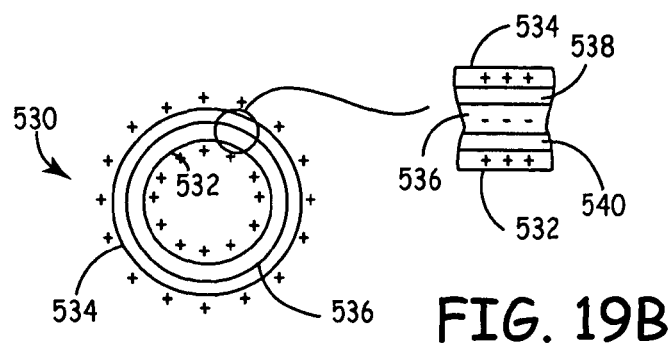
FIG. 19B is a sectional end view of the stent of FIG. 19A with the section taken along line B-B of FIG. 19A, in which the insert depicts the layered structure of the stent.

A further embodiment of an implant, such as a stent, is shown in FIGS. 19A and 19B that introduce a treatment approach based on altering the chemistry within the vessel through the electrical properties at the surface of the stent. Device 530 in FIGS. 19A and 19B has a positive surface charge along inner surface 532 and outer surface 534, which is balanced with an internal negative charge along a layer 536, shown in FIG. 19B. Thus, the structure has the form of a capacitor with appropriately placed insulating layers 538, 540 to prevent short circuit. A controller 542 can be used to control the operation of the device. Controller 542 can incorporate electrical components as discussed above.

The positive charge attracts anions and repels cations, such as calcium cations, to inhibit their deposition on the surface of the device as part of a calcification process or other undesirable process. If desired, the charge can be reversed to have a negative surface charge that attracts cations and repel anions, which can prevent other deposits onto the surface, such as positively charged proteins from the blood. Similarly, the inner and outer surface of the stent can have opposite charges from each other with an inner surface that is either positive or negative as selected through the reduction in the number of layers. As shown in FIGS. 19A and 19B, the device is a vascular stent. However, a surface charge can be applied based on this description for any reasonable implant including, for example, other types of implants described herein. Thus, undesirable deposits can be inhibited based on the use of a surface charge. Alternatively, the stent of FIGS. 19A and 19B can be used as a diagnostic tool by detecting the ionic strength, i.e., the amounts of positive ions and negative ions, in the blood through changes in the resulting capacitance of the stents.

Figure 20A:
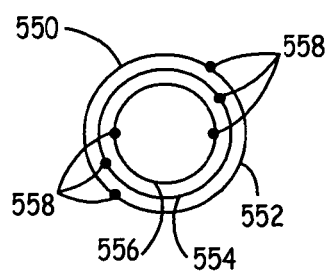
FIG. 20A is an end view of a stent with a layered structure and optional lever arms to facilitate separation of the layers following deployment.
Figure 20B:
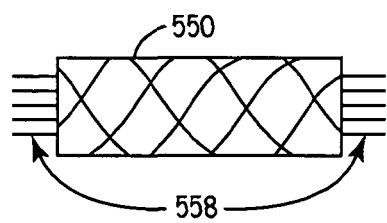
FIG. 20B is a side view of the layered stent of FIG. 20A.

Another embodiment of a stent is shown in FIGS. 20A and 20B. In this embodiment, stent 550 has a plurality of layers 552, 554, 556. Each layer can be formed appropriately similarly to a conventional stent with an appropriately thinner wall thickness, in which the layers are then placed inside subsequent layers. The layers can be separated from each other. As shown in FIGS. 20A and 20B, each layer has lever arms 558 to facilitate removal of a layer from the interior of the combined structure. The removal of an interior layer can remove associated deposits and or expose a fresh drug coated surface to the blood flow. The stent walls can be formed to fold upon pulling on a lever arm. Suitable grippers can be delivered from a catheter with examples of suitable gripper described in U.S. Pat. No. 6,695,866 to Keune et al., entitled "Mitral and Tricuspid Valve Repair," incorporated herein by reference. Since the layers of the device are designed for removal, the surface of the device can be designed to attract undesirable components of the associated bodily fluids, such as plaque or emboli, for collection on the surface. Then, the undesirable composition can be removed along with the removal of the layer of device structure. While the stent is shown with three layers, other embodiments can have two layers or more than three layers, such as four or more layers, with the thicknesses reduced accordingly. The multiple layers provide structural integrity for deployment that may not be needed subsequent to deployment.

Figure 21A:
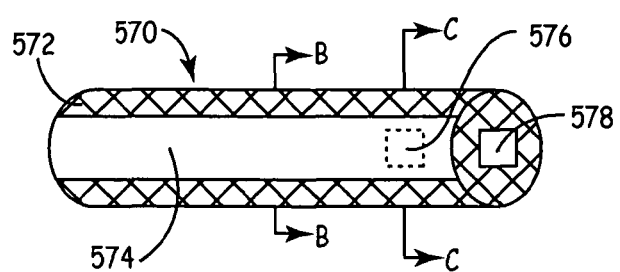
FIG. 21A is a side perspective view of a stent configured for drug delivery controlled with a MEMS structure.
Figure 21B:
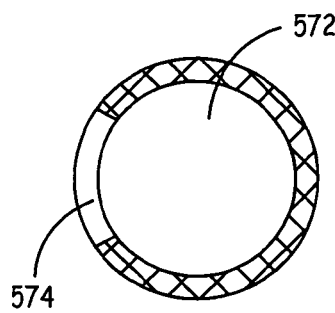
FIG. 21B is an end sectional view of the stent of FIG. 21A with the section taken along line B-B of FIG. 21A.
Figure 21C:
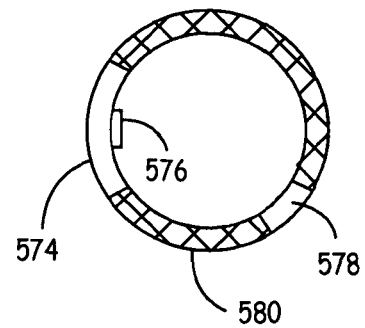
FIG. 21C is an end sectional view of the stent of FIG. 21A with the section taken along line C-C of FIG. 21A.

A general MEMS structure for an implanted medical device is shown schematically in FIG. 8. A specific embodiment incorporated into a stent is shown in FIGS. 21A-21C. Referring to FIGS. 21A-21C, stent 570 comprises a support structure 572, a reservoir 574, a MEMS structure 576, and a controller 578 electrically connected to MEMS structure 576 with a wire 580 or the like. Reservoir 574 comprises a reservoir with the desired drug/bioactive agent within the reservoir. As shown in FIGS. 21A-21C, reservoir 574 extends over only a portion of the circumference while the remaining portions of the stent can be a mesh, weave, braid or the like, although other configurations can be used. Walls of reservoir 574 can be formed from spring metals, polymers or other materials suitable for use in a stent, as described above. The MEMS structure is shown in FIG. 21C, and can take the specific forms described above in the context of FIG. 10. Suitable electronics for the controller are described above.

Aneurysms are an abnormal blood filled dilation of the wall of an artery due to a defect or disease of the blood vessel. Aneurysms can develop quickly and can result in a hemorrhage that can lead to stroke or even death. Aneurysms can occur in the aorta and can be very serious. Instrumented implants can be placed within or in close proximity to a vessel to detect and/or monitor for aneurysms. For example, stents described above can be adapted for this purpose. Similarly, external sensors connected to a comparable monitoring system can also be used for detecting aneurysms.

Figure 22A:
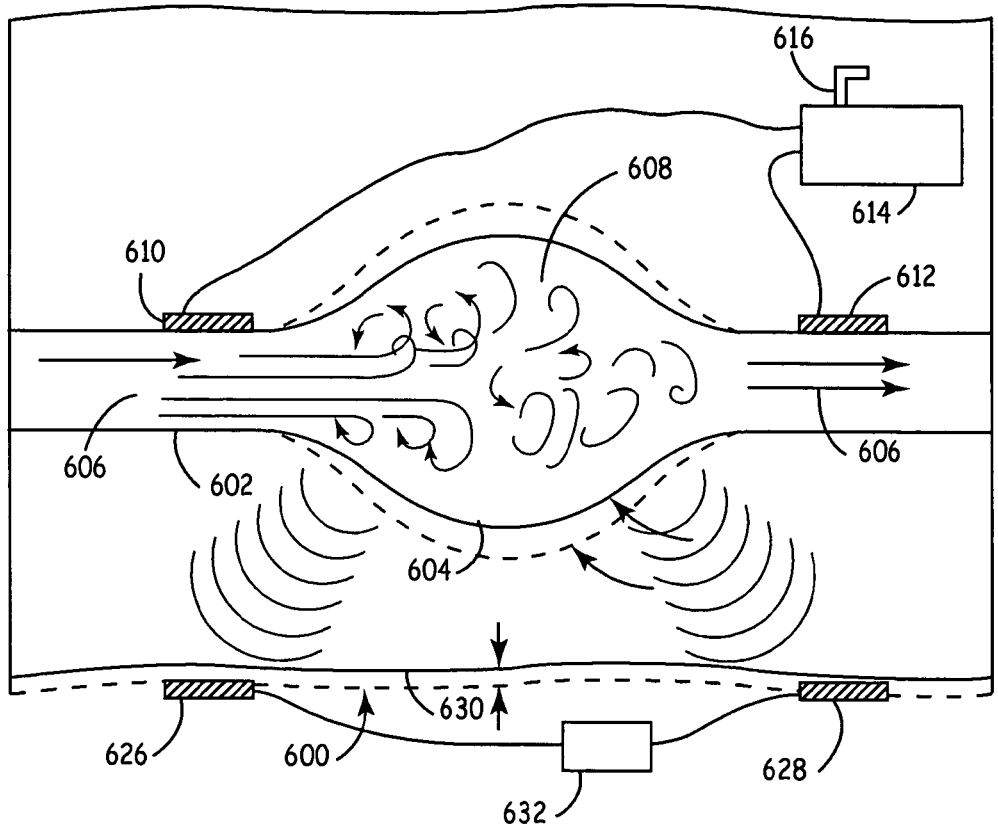
FIG. 22A is a schematic cross section of a body portion with sensors configured to detect aneurysms, with two stent-based sensors deployed within the vessel and two sensors deployed on the skin.

Suitable systems for detecting aneurysms are described further within FIG. 22A. These detection systems generally are based on either variations in blood pressure as a function of time, based on acoustics related to blood flow, accelerometer measurements of skin motion responding to blood flow and the like. Referring to FIG. 22A, a schematic cross section of a body part 600 of the patient, such as a limb or neck, with a blood vessel 602 is shown schematically along with corresponding devices. Blood vessel 602 has an aneurysm 604. Blood flow can be laminar 606 away from aneurysm 604 and turbulent 608 at the aneurysm. Implanted sensors 610, 612 can be mounted separately on a stent or the like. Sensors 610, 612 are generally spaced apart from each other a suitable distance for meaningful measurements at different locations of the vessel. Sensors 610, 612 are operably connected to electronics 614 with a wired and/or wireless connection. While shown in FIG. 22A with a single electronics module, sensors 610, 612 can be operably connected to separate electronics modules that independently transmit sensor measurements external to the patient. Electronics 614 can be mounted on a stent along with or separately from a sensor 610 or 612, and electronics 614 comprises an antenna 616 that can transmit information on the measurements of the sensors external to the body. Additional sensors can be used as desired. Suitable stents and electronics are described above with respect to FIGS. 2-6.

Additionally or alternatively, sensors 626, 628 are mounted on skin 630. Sensors 628, 630 can be operably connected to electronics 632 with a wireless or wired connection for collecting, transmitting and/or analyzing the measurements of sensors 626, 628. While a single electronics module is shown connected to sensors 626, 628, each sensor can be operably connected with a separate electronics module. While FIG. 22A shows two implanted sensors or two skin mounted sensors, more than two sensors can be implanted or skin mounted, such as three, four or more sensors.

Figure 22F:
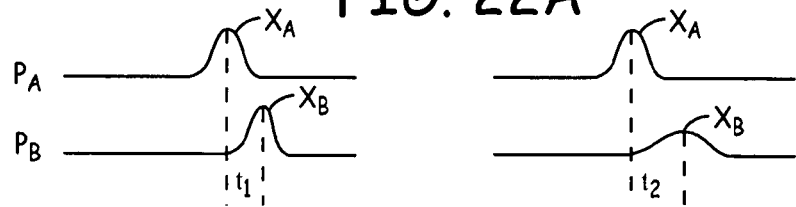
FIG. 22F is a plot of pressure pulses measured in a blood vessel with two sensors A and B with sensor B being downstream form sensor A, such as shown in FIG. 22A, in which the right plot is at a later time relative to the left plot indicating the development of an aneurysm at the time $t_2$ that was not present at time $t_1$.
Figure 22B:
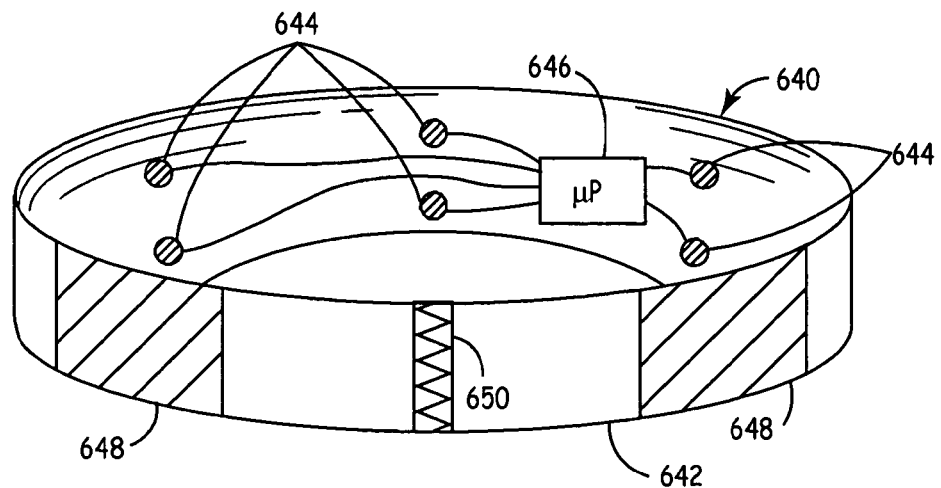
FIG. 22B is a perspective view of a band to be worn by a patient with sensors suitable for detecting aneurysms.
Figure 22C:
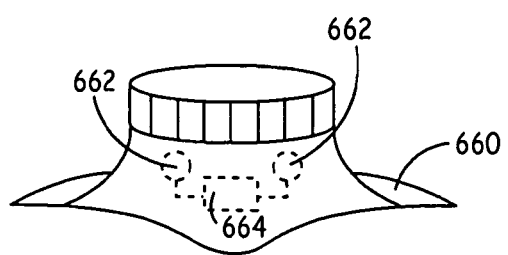
FIG. 22C is a fragmentary view of an article of clothing fitted with sensors suitable for detecting aneurysms.

Additionally or alternatively, sensors can be placed on a collar or other band such that they are in contact with the skin when the band is worn by the patient. Referring to FIG. 22B, collar 640 comprises a band 642, sensors 644 and an electronic module 646 operably connected to sensors 644 with a wired or wireless connection. Band 642 can comprise one or more elastic portions 648 as well as an optional closure 650 that can be used to open the collar to facilitate placement on the patient. Optional closure can comprise, for example, a hook-and-loop fastener, a zipper, snaps, buttons or other suitable closures. Suitable sensors and electronics modules are described above with respect to FIG. 22A. Rather than using a band, the sensors can be similarly incorporated into an article of clothing. Referring to the fragmentary view in FIG. 22C, a sweater/shirt 660 is shown with sensors 662 and electronics module 664 with a wired or wireless connection with sensors 662. While six sensors are shown in FIG. 22B and two sensors are shown in 20C, the number and placement of sensors can be determined to obtain the desired measurements upon placement within the patient. Similarly, the sensors can be repositionable, for example, with a hook-and-look fastener or the like, such that a health care professional can locate the sensors at suitable locations to obtain the desired measurements.

Figure 22E:
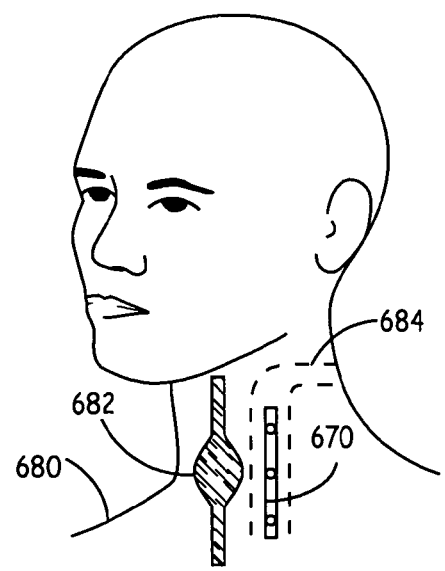
FIG. 22E is a schematic view of the neck of a patient with an implanted device of FIG. 22D placed near a carotid artery.
Figure 22D:
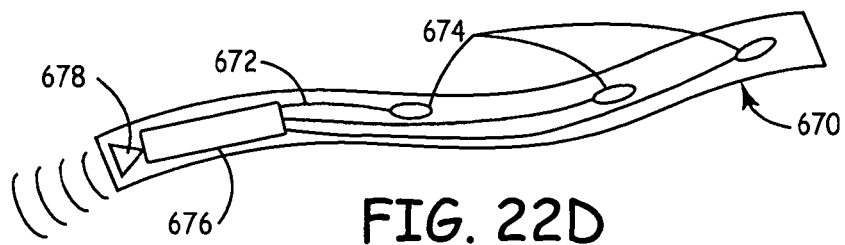
FIG. 22D is a side view of an implantable device configured with sensors suitable for detecting aneurysms in nearby blood vessel(s).

As an addition or an alternative to the placement of sensors in a blood vessel or on the skin, the sensors can be implanted at a suitable location to sense the pulse of the vessel of concern. Referring to FIG. 22D, an implantable sensing device 670 comprises a flexible support 672, sensors 674 and electronics module 676 with wired or wireless communication with sensors 674. Electronics module 676 comprises an antenna 678. Flexible support 672 can comprise an elastomeric biocompatible polymer, such as a silicon polymer or a polyurethane, although metals or combinations of metals and polymer can be used. In some embodiments, a rigid support can be used as an alternative to a flexible support, which can be formed, for example, from metal, polymer, ceramics or combinations thereof. Suitable sensors 674 and electronics module 676 are described with respect to FIGS. 22A-C. Referring to FIG. 22E, an embodiment of implantable sensing device 670 is depicted implanted within the neck 680 of a patient with suitable placement to measure pulsing of a carotid artery 682. Device 670 can be implanted in a surgical procedure or with a less invasive procedure through a small incision using a cannula or the like, which opens up a small channel 684.

As noted above, the sensors can be based on a range of principles. Referring to FIG. 22F, pressure measurements from two sensors are depicted. The pressure at the downstream sensor is labeled A, and the pressure at an upstream sensor is labeled B. $X_A$ and $X_B$ denote the peak pressure values from the two sensors, respectively, and a time t represents the time delay between the two peak measurements. The measurements of a normal vessel are depicted in the left diagram, and the measurements for a vessel with a potential aneurysm is depicted in the right diagram. If the vessel is normal, the peak pressure values are approximately equal. If the vessel has an aneurysm, the pulse is delayed relative to a normal vessel ($t_2 > t_1$), and the peak height is lowered since the presence of an aneurysm slows the propagation of the pressure pulse and dissipates some for the force of the pulse resulting in a lower pressure reading.

Figure 22G:
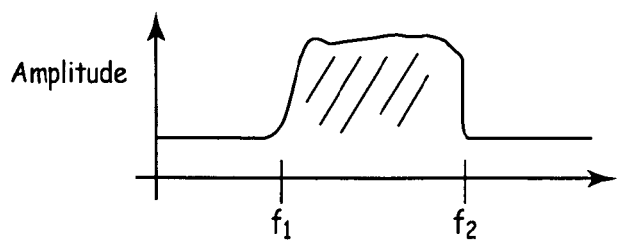
FIG. 22G is a schematic depiction of a plot of acoustic measurements in a blood vessel as a function of frequency.
Figure 22H:
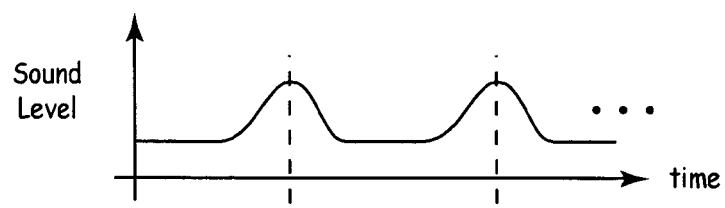
FIG. 22H is a schematic depiction of a plot of acoustic measurements as a function of time showing two pulses of the vessel.
Figure 22I:
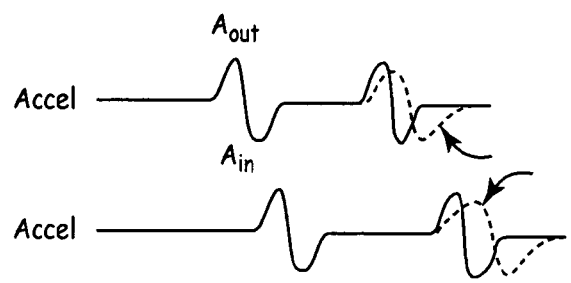
FIG. 22I is a schematic depiction of measurements of an accelerometer configured to measure responses in nearby tissue or skin as a result of a vessel pulsing.

Furthermore, acoustic sensors can be used. Referring to FIGS. 22G and 22H, the acoustic measurements can be analyzed as a function of frequency (FIG. 22G) and/or time (FIG. 22H). If an aneurysm is present, the acoustic measurements can have characteristic plots indicative of a hiss that can be deduced from the frequency or time measurements. The hiss can be a result of turbulence of the flow due to the presence of the aneurysm. Accelerometers can be used to replace the acoustic sensors. The use of a plurality of sensors increases the likelihood of "hearing" the sounds of an aneurysm. Accelerometers measure movement associated with the pulse of the vessel. There is a movement outward from the vessel with the pulse followed with a return to the original position. Accelerometer measurements are shown schematically in FIG. 22I. The readings of two different accelerometer signals are shown in FIG. 22I with one being above the other. The presence of an aneurysm can be detected either by differences between the measurements of the two sensors and/or through changes in the measurements over time, as noted with the arrows in the figure.

The embodiments described above are intended to be illustrative and not limiting. Additional embodiments are within the claims below. Although the present invention has been described with reference to specific embodiments, workers skilled in the art will recognize that changes may be made in form and detail without departing from the spirit and scope of the invention. In addition, the terms including, comprising and having as used herein are intended to have broad non-limiting scope. References cited above are incorporated to the extent that they are not inconsistent with the explicit disclosure herein.

What is claimed is:

1. A prosthetic vessel, comprising:
    a support structure, including a biocompatible material and having a structure suitable for replacement of a portion of a mammalian vessel;
    a sensor, supported by the support structure, configured to perform a measurement of a physiological parameter;
    an implantable wireless communication system, in communication with the sensor, configured to transmit information about the measurement of the physiological parameter;
    a treatment transducer, supported by the support structure, configured to deliver a treatment response; and
    an implantable microprocessor having an associated memory, in communication with the sensor, the implantable wireless communication systems, and the treatment transducer, the implantable microprocessor configured to control the treatment response based upon information about the measurement of the physiological parameter and a treatment protocol stored in the memory, and reprogram the memory with a new treatment protocol received through the implantable wireless communication system.

2. The prosthetic vessel of claim 1, further comprising:
    an implantable battery coupled with and configured to power the implantable microprocessor;
    wherein the implantable wireless communication system comprises an antenna assembled on a chip.

3. The prosthetic vessel of claim 1, further comprising:
    a second sensor, supported by the structure, configured to perform a second measurement of a physiological parameter,
    wherein the implantable microprocessor controls the treatment response based upon information about the measurements of one or more physiological parameters obtained by the sensor and the second sensor.

4. The prosthetic vessel of claim 1, wherein the support structure comprises a structure including fasteners configured to attach to a mammalian vessel.

5. The prosthetic vessel of claim 1, wherein the support structure comprises a metal.

6. The prosthetic vessel of claim 1, wherein the support structure comprises a polymer.

7. The prosthetic vessel of claim 2, wherein the implantable wireless communication system, the implantable microprocessor, and the implantable battery are coupled with the support structure.

8. The prosthetic vessel of claim 1, further comprising a drug delivery device with a delivery rate controlled by the implantable microprocessor.

9. A method, comprising:
sensing a measurement of a physiological parameter using a sensor associated with a prosthetic vessel;
wirelessly transmitting, from the prosthetic vessel, information about the measurement of the physiological parameter using a wireless communication system;
delivering a treatment response based upon information about the measurement of the physiological parameter and a stored treatment protocol using a treatment transducer;
controlling the treatment response based upon information about the measurement of the physiological parameter and the treatment protocol stored in a memory of an implantable microprocessor in communication with the sensor, the wireless communication system and the treatment transducer; and
reprogramming the stored treatment protocol with a new treatment protocol received through the implantable wireless communication system.

10. The method of claim 9, further comprising sensing a second measurement of a physiological parameter using a second sensor associated with the prosthetic vessel.

11. The method of claim 10, wherein delivering the treatment response includes delivering a treatment response based upon information about the measurements of one or more physiological parameters obtained by the sensor and the second sensor.

12. The method of claim 9, further comprising attaching portions of the prosthetic vessel to a mammalian vessel using one or more fasteners.

13. The method of claim 9, further comprising supporting the prosthetic vessel using a support structure comprising a biocompatible material.

14. The method of claim 9, wherein wirelessly transmitting information includes using an antenna assembled on a chip.

15. The method of claim 9, wherein delivering the treatment response includes delivering a drug at a controlled rate.

* * * * *